US008802092B2

(12) United States Patent
Nishimoto et al.

(10) Patent No.: US 8,802,092 B2
(45) Date of Patent: Aug. 12, 2014

(54) MESOTHELIOMA THERAPEUTIC AGENT

(75) Inventors: Norihiro Nishimoto, Minohi (JP);
Tadamitsu Kishimoto, Tondabayashi (JP); Yasuo Adachi, Suita (JP); Koichi Takayama, Fukuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/081,126

(22) Filed: Apr. 10, 2008

(65) Prior Publication Data
US 2008/0274106 A1 Nov. 6, 2008

Related U.S. Application Data

(63) Continuation of application No. 10/575,455, filed as application No. PCT/JP2004/015674 on Oct. 15, 2004, now abandoned.

(30) Foreign Application Priority Data

Oct. 17, 2003 (JP) ................................. 2003-358152

(51) Int. Cl.
*A61K 39/395* (2006.01)
(52) U.S. Cl.
USPC ..................................... 424/133.1; 424/143.1
(58) Field of Classification Search
USPC ........................................... 424/133.1, 143.1
See application file for complete search history.

(56) References Cited

U.S. PATENT DOCUMENTS

| 5,670,373 | A | 9/1997 | Kishimoto |
| 5,888,510 | A | 3/1999 | Kishimoto et al. |
| 6,723,319 | B1 | 4/2004 | Ito et al. |
| 2002/0187150 | A1 | 12/2002 | Mihara et al. |
| 2004/0115197 | A1 | 6/2004 | Yoshizaki et al. |
| 2004/0161426 | A1 | 8/2004 | Trikha et al. |
| 2005/0090453 | A1 | 4/2005 | Carter et al. |
| 2006/0094645 | A1 | 5/2006 | Lawless |
| 2006/0292147 | A1 | 12/2006 | Yoshizaki et al. |

FOREIGN PATENT DOCUMENTS

| CN | 1297357 A | 5/2001 |
| EP | 0 409 607 A2 | 1/1991 |
| EP | 0 628 639 A1 | 12/1994 |
| EP | 0 791 359 A1 | 8/1997 |
| EP | 1 074 268 A1 | 2/2001 |
| EP | 1 334 731 A1 | 8/2003 |
| JP | 8-245414 A | 9/1996 |
| WO | WO 96/40966 A1 | 12/1996 |
| WO | WO 01/42484 A1 | 6/2001 |
| WO | WO 2004/096273 A1 | 11/2004 |

OTHER PUBLICATIONS

Fundamental Immunology 242 (William E. Paul, M.D. ed., 3d ed. 1993).*
Sato et al. (Can. Res. 53:851-856 (1993)).*
Nishimoto et al. (Ann Rheum. Dis. 59(Suppl 1):i21-i27 (2000)).*
Bielefeldt-Ohmann et al. (Can. Immunol. Immunother. 40:241-250 (1995)).*
Office Action received May 9, 2008, in counterpart Chilean Application 2654-2004, 6 pages.
Bielefeldt-Ohmann, H., et al., "Interleukin-6 involvement in mesothelioma pathobiology: inhibition by interferon α immunotherapy", Cancer Immunol. Immunother., vol. 40, pp. 241-250 (1995).
Suzuki, H., et al., "Anti-human interleukin-6 receptor antibody inhibits human myeloma growth in vivo", Euro. J. Immunol., vol. 22, pp. 1989-1993 (1992).
Nakano, T., et al,. "Interleukin-6 and its relationship to clinical parameters in patients with malignant pleural mesothe lioma", British Journal of Cancer, vol. 77, No. 6, pp. 907-912 (1998).
Higashihara, M., M.D., Increased Secretion of Interleukin-6 in Malignant Mesothelioma Cells from a Patient with Marked Thrombocy tosis, Cancer, vol. 70, No. 8, pp. 2105-2108 (1992).
Tamura et al., "Soluble interleukin-6 receptor triggers osteoclast formation by interleukin 6," Proc. Natl. Acad. Sci. USA, Dec. 1993, 90:11924-11928.
Supplementary European Search Report dated Jun. 15, 2009, in corresponding European Patent Application EP 04792816.3, 4 pages.
Adachi et al., "Interleukin-6 induces both cell growth and VEGF production in malignant mesotheliomas," Int. J. Cancer, Sep. 15, 2006, 119(6):1303-1311.
Mihara et al., "Influences of anti-mouse interleukin-6 receptor antibody on immune responses in mice," Immunology Letters, Dec. 3, 2002, 84(3):223-229.
Monti et al., "Intrapleural Production of Interleukin 6 during Mesothelioma and Its Modulation by γ-Interferon Treatment," Cancer Research, Aug. 15, 1994, 54(16):4419-4423.
Naka et al., "The paradigm of IL-6: from basic science to medicine," Arthritis Research, Current Science, May 9, 2002, 4(Suppl.3):S233-S242.
Office Action in corresponding Colombian patent application, 3 pages.
Trikha et al. "Targeted Anti-Interleukin-6 Monoclonal Antibody therapy for Cancer: A Review of the Rationale and Clinical Evidence," Clinical Cancer Research, Oct. 15, 2003, 9:4653-4665.

(Continued)

*Primary Examiner* — Lynn Bristol
(74) *Attorney, Agent, or Firm* — Foley & Lardner LLP

(57) ABSTRACT

The present invention provides a mesothelioma therapeutic agent containing an interleukin-6 (IL-6) antagonist such as antibody to IL-6 receptor (IL-6R), and a mesothelioma cell growth inhibitor containing an IL-6 antagonist such as antibody to IL-6R.

27 Claims, 17 Drawing Sheets

(56) References Cited

OTHER PUBLICATIONS

Tsujinaka et al,. "Muscle wasting and IL-6," Basic Appl. Myol., 1998, 8(5):361-370.
Office Action issued on Aug. 24, 2010, in corresponding JP 2005-514876, 4 pages.
Imazeki et al., "IL-6 functions in cynomolgus monkeys blocked by a humanized antibody to human IL-6 receptor," International Journal of Immunopharmacology, 1998, 20(7):345-357.
McLaren et al., "New chemotherapeutics in malignant mesothelioma: effects on cell growth and IL-6 production," Cancer Chemother. Pharmacol., 2000, 45:502-508.
Supplementary Novelty Search Report mailed Jun. 18, 2009, in corresponding GC patent application No. GCC/P/2004/3904, 4 pages.
Examination Report dated Jun. 1, 2009, in corresponding GC patent application No. GCC/P/2004/3904, 4 pages.
Bellomo, R., "The Cytokine Network in the Critically Ill," Anaesthesia and Intensive Care, Aug. 1992, 20(3):288-302.
Guice et al., "Anti-Tumor Necrosis Factor Antibody Augments Edema Formation in Caerulein-Induced Acute Pancreatitis," Journal of Surgical Research, 1991, 51:495-499.
Hocking et al., "Mechanisms of Pulmonary Edema Induced by Tumor Necrosis Factor-α," Circulation Research, 1990, 67:68-77.
Murata et al., "Development mechanism and pathophysiology: Possible Implication of Cytokines in the Pathophysiology of Acute Pancreatitis," The Saishin-Igaku, Special Issue: A new point of view in pancreatic diseases, Nov. 1992, 47(11):49-56, with English translation, 17 pages.
Nowak et al., "Combination of Methotrexate and Prednizone Decreases Circulating Concentrations of Interleukin 1β and Interleukin 6 in Patients with Rheumatoid Arthritis: Poor Correlation of Cytokine Supression with Clinical Improvement," International Journal of Immunopathology and Pharmacology, 1999, 12(1):13-21.
Office Action dated Mar. 8, 2011, in corresponding EP 04 792 816.3, 7 pages.
Rose-John et al., "Interleukin-6 biology is coordinated by membrane-bound and soluble receptors: role in inflammation and cancer," Journal of Leukocyte Biology, Aug. 2006, 80(2):227-236.
Ulich et al., "Intratracheal Injection of Endotoxin and Cytokines," American Journal of Pathology, May 1991, 138 (5):1097-1101.
Hirata et al., "Characterization of IL-6 Receptor Expression by Monoclonal and Polyclonal Antibodies," J. Immunol., Nov. 1, 1989, 143(9):2900-2906.

\* cited by examiner

Fig.3
(A)
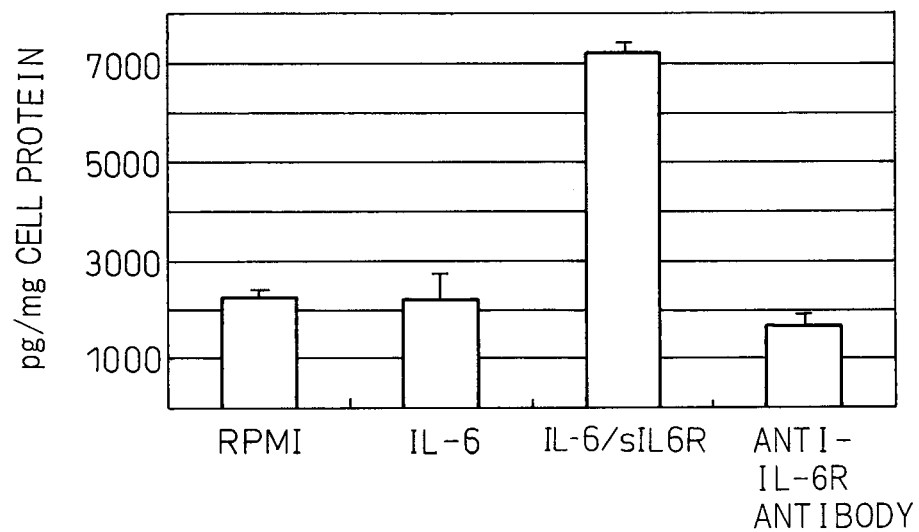
(B)
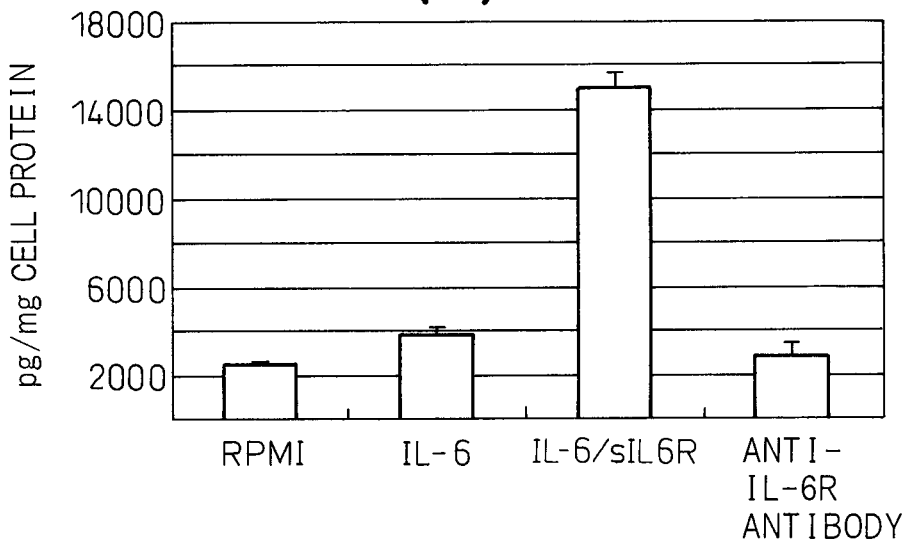

Fig. 11
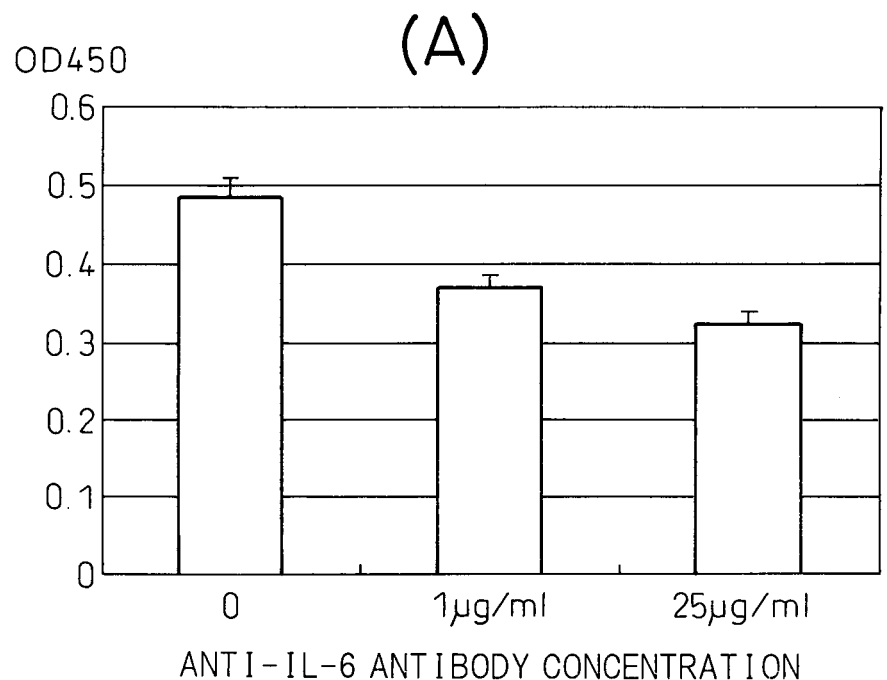
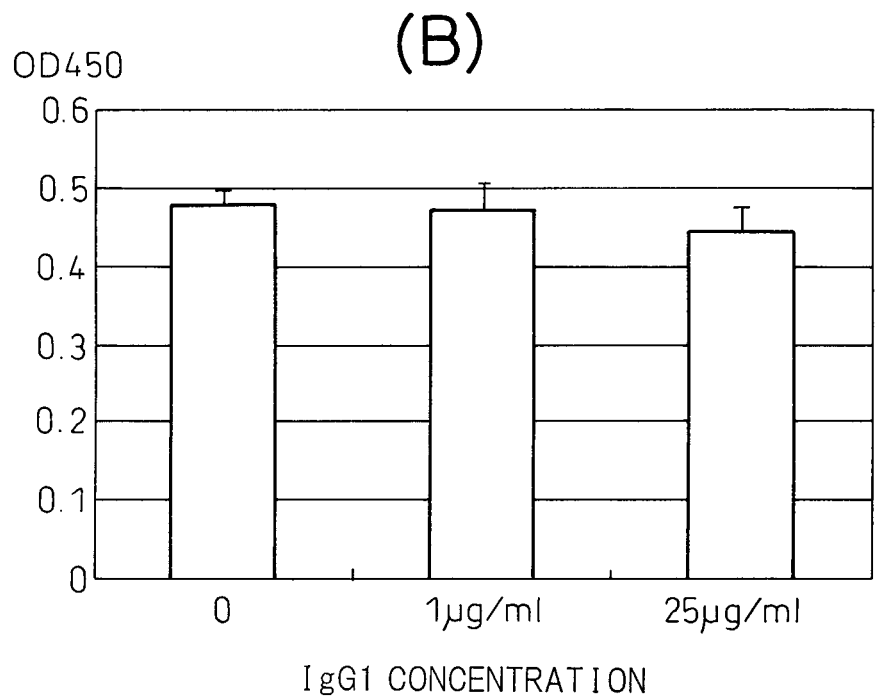

MESOTHELIOMA THERAPEUTIC AGENT

CROSS REFERENCE TO RELATED APPLICATIONS

This application is a Continuation of U.S. application Ser. No. 10/575,455 filed Aug. 9, 2006, now abandoned, which is the U.S. National Stage application of PCT/JP2004/015674, filed Oct. 15, 2004, which claims the benefit of Japanese patent application JP 2003-358152, filed Oct. 17, 2003. The entire contents of each of the aforementioned applications are incorporated herein by reference.

TECHNICAL FIELD

The present invention relates to a novel mesothelioma therapeutic agent and mesothelioma cell inhibitor.

BACKGROUND ART

Mesothelioma is a tumor that occurs in the mesothelium that covers the surface of the pleura, peritoneum and pericardium that respectively envelop the organs of the chest cavity such as the lungs and heart, and abdominal organs such as the digestive tract and liver. In the case of diffuse pleural mesothelioma, chest pain is caused by invasion of the intercostals nerves on the side of the chest wall pleura, and respiratory and circulatory disorders may occur due to tumor growth and accumulation of pleural fluid in the pleura on the organ side (Takagi, Journal of Clinical and Experimental Medicine, (March Supplement), "Respiratory Diseases", pp. 469-472, 1999). There is eventually proliferation into the adjacent mediastinal organs, progressing to direct invasion of the heart or development into the abdominal cavity by means of the diaphragm, or there may be development outside the chest cavity as a result of additional lymphatic or circulatory metastasis (ibid).

In the U.S., diffuse pleural mesothelioma is reported to occur in 3,000 persons annually, the number of cases began to increase prominently in the 1980s, and is frequently observed in men in their sixties, with the incidence in men being roughly five times that in women (Takagi, Journal of Clinical and Experimental Medicine (March Supplement), "Respiratory Diseases", pp. 469-472, 1999). According to recent reports in the U.S. and Europe, the incidence of mesothelioma is demonstrating a rapidly increasing trend, and based on epidemiological statistics from the U.K. in 1995, the number of deaths from mesothelioma is predicted to continue to increase over the next 25 years, and in the worst possible scenario, has been indicated as having a risk to the extent of accounting for 1% of all deaths among men born in the 1940s (Nakano, Respiration, Vol. 18, No. 9, pp. 916-925, 1999).

Numerous different classifications of the clinical disease stages have been used for mesothelioma, and since the methods for classifying the disease stage used differ, previous therapeutic reports on mesothelioma have encountered difficulties when comparing the results of treatment (Nakano, Respiration, Vol. 18, No. 9, pp. 916-925, 1999). An international TNM classification for malignant pleural mesothelioma in 1995 by the International Mesothelioma Interest Group (IMIG) (Nakano, Respiration, Vol. 18, No. 9, pp. 916-925, 1999).

In addition, malignant mesothelioma has a causative relationship with exposure to asbestos, and this has also been demonstrated in animal experiments (Tada, Journal of Clinical and Experimental Medicine (March Supplement), "Respiratory Diseases", pp. 406-408, 1999). Asbestos that has been inhaled into the respiratory tract reaches a location directly beneath the pleura where a tumor eventually develops due to chronic irritation for at least about 20 years, and this tumor spreads in a thin layer over the entire surface of the pleura (Takagi, Journal of Clinical and Experimental Medicine (March Supplement), "Respiratory Diseases", pp. 469-472, 1999). Consequently, although malignant mesothelioma is classified as an asbestos-related disease, not all malignant mesothelioma is caused by asbestos, and well-documented exposure is only observed in about half of all patients (Tada, Journal of Clinical and Experimental Medicine (March Supplement), "Respiratory Diseases", pp. 406-408, 1999).

Malignant pleural mesothelioma is resistant to treatment, is associated with an extremely poor prognosis, and requires that countermeasures be taken immediately (Nakano, Respiration, Vol. 18, No. 9, pp. 916-925, 1999). For example, although the folic acid antagonist, methotrexate (MTX), has a satisfactory efficacy rate of 37% in large-dose single treatment in combination with leucovin, its use has not proliferated due to the technical difficulty associated with application to mesothelioma that causes retention of a large amount of pleural fluid (Nakano, Journal of Clinical and Experimental Medicine (March Supplement), "Respiratory Diseases", pp. 570-573, 2003). In addition, although pleuropulmonary excision and pleurectomy are performed for diffuse pleural mesothelioma, there is increased susceptibility to relapse following treatment, and the post-surgical local relapse rate in particular is high at 35-43% (Takagi, Journal of Clinical and Experimental Medicine (March Supplement), "Respiratory Diseases", pp. 469-472, 1999).

Numerous human mesothelioma cell lines and several mouse mesothelioma cell lines are known to express IL-6 in vitro, and in mice transplanted with mouse mesothelioma cell line AB22, which expresses a high level of IL-6, IL-6 has been reported to be detected in serum prior to cancer cell growth, clinical symptoms and changes in peripheral blood lymphocyte tissue (Bielefeldt-Ohmann, Cancer Immunol. Immunother. 40: 241-250, 1995). In addition, serum IL-6 levels in patients with malignant pleural mesothelioma are higher in comparison with pulmonary adenoma patients complicated with pleural effusion, and with respect to thrombocytosis, which is one of the clinical symptoms of malignant pleural mesothelioma, there is known to be a remarkable correlation between serum IL-6 levels and platelet counts (Nakano, British Journal of Cancer 77(6): 907-912, 1998). Moreover, the tumor cells of pleural mesothelioma patients express high levels of IL-6, and IL-6 levels in the serum have been reported to increase prior to death (Higashihara, Cancer, Oct. 15, 1992, Vol. 70, No. 8, pp. 2105-2108).

As a result of administering rat anti-mouse IL-6 antibody (6B4) to mouse transplanted with AB22 at the rate of twice a week, Bielefeldt-Ohmann, et al. reported that effects were observed that considerably diminished the onset and progression of clinical symptoms (Bielefeldt-Ohmann, Cancer Immunol. Immunother. 40: 241-250, 1995). However, according to a report by Bielefeldt, anti-IL-6 antibody does not have a direct growth inhibitory effect on AB22 in vitro, there were no differences observed in the postmortem appearances of mice treated with anti-IL-6 antibody and those not treated with said antibody, and tumor masses of considerable size were observed even in the treated mice (Bielefeldt-Ohmann, Cancer Immunol. Immunother. 40: 241-250, 1995). Namely, growth inhibition of mesothelioma by anti-IL-6 antibody has not been known both in vitro and in vivo.

Takagi, Journal of Clinical and Experimental Medicine (March Supplement), "Respiratory Diseases", pp. 469-472, 1999

Nakano, Respiration, Vol. 18, No. 9, pp. 916-925, 1999

Tada, Journal of Clinical and Experimental Medicine (March Supplement), "Respiratory Diseases", pp. 406-408, 1999

Nakano, Journal of Clinical and Experimental Medicine (March Supplement), "Respiratory Diseases", pp. 570-573, 2003

Bielefeldt-Ohmann, Cancer Immunol. Immunother. 40: 241-250, 1995

Higashihara, Cancer, Oct. 15, 1992, Vol. 70, No. 8, pp. 2105-2108

DISCLOSURE OF THE INVENTION

IL-6 antagonists were not known to act directly on mesothelioma and demonstrate growth inhibitory effects. An object of the present invention is to provide a novel mesothelioma therapeutic agent (mesothelioma cell growth inhibitor) that contains an IL-6 antagonist as its active ingredient.

As a result of conducting extensive studies to develop a novel mesothelioma therapeutic agent that inhibits the growth of mesothelioma cells, the inventor of the present invention obtained the novel finding that the growth of mesothelioma cells can be inhibited by inhibiting or interrupting signal transmission relating to IL-6, thereby leading to completion of the present invention.

Thus, the present invention provides a mesothelioma therapeutic agent that contains an interleukin-6 (IL-6) antagonist as its active ingredient.

In addition, the present invention also provides a growth inhibitor against mesothelioma cells that contains an interleukin-6 (IL-6) antagonist as its active ingredient.

The aforementioned mesothelioma is, for example, pleural mesothelioma, and more specifically, malignant pleural mesothelioma. Diffuse pleural mesothelioma is included in malignant pleural mesothelioma.

The aforementioned IL-6 antagonist is, for example, an antibody to IL-6 or an antibody to IL-6 receptor, and preferably a monoclonal antibody to IL-6 receptor. The aforementioned antibody to IL-6 receptor is particularly preferably a monoclonal antibody to human IL-6 receptor such as PM-1 antibody, or a monoclonal antibody to mouse IL-6 receptor such as MR16-1 antibody. The aforementioned antibody to IL-6 receptor is preferably a recombinant antibody.

The aforementioned antibody to IL-6 receptor may be a chimeric antibody, humanized antibody or human antibody. In the present invention, a particularly preferable antibody is humanized PM-1 antibody.

The present invention can also be in the forms indicated below.

(1) The use of an interleukin-6 (IL-6) antagonist to produce a mesothelioma therapeutic agent.
(2) The use according to (1) above in which the mesothelioma is pleural mesothelioma.
(3) The use according to (2) above wherein the pleural mesothelioma is malignant pleural mesothelioma.
(4) The use according to any of (1) through (3) above wherein the IL-6 antagonist is an antibody to IL-6 receptor.
(5) The use according to (4) above wherein the antibody to IL-6 receptor is a monoclonal antibody to IL-6 receptor.
(6) The use according to (4) above wherein the antibody to IL-6 receptor is a monoclonal antibody to human IL-6 receptor.
(7) The use according to (4) above wherein the antibody to IL-6 receptor is a monoclonal antibody to mouse IL-6 receptor.
(8) The use according to any of (4) through (7) above wherein the antibody to IL-6 receptor is a recombinant antibody.
(9) The use according to (6) above wherein the monoclonal antibody to human IL-6 receptor is PM-1 antibody.
(10) The use according to (7) above wherein the monoclonal antibody to mouse IL-6 receptor is MR16-1 antibody.
(11) The use according to any of (4) through (10) above wherein the antibody to IL-6 receptor is a chimeric antibody, humanized antibody or human antibody to IL-6 receptor.
(12) The use according to (11) above wherein the humanized antibody to IL-6 receptor is humanized PM-1 antibody.
(13) The use of an interleukin-6 (IL-6) antagonist to produce a growth inhibitor against mesothelioma cells.
(14) The use according to (13) above in which the mesothelioma is pleural mesothelioma.
(15) The use according to (14) above wherein the pleural mesothelioma is malignant pleural mesothelioma.
(16) The use according to any of (13) through (15) above wherein the IL-6 antagonist is an antibody to IL-6 receptor.
(17) The use according to (16) above wherein the antibody to IL-6 receptor is a monoclonal antibody to IL-6 receptor.
(18) The use according to (16) above wherein the antibody to IL-6 receptor is a monoclonal antibody to human IL-6 receptor.
(19) The use according to (16) above wherein the antibody to IL-6 receptor is a monoclonal antibody to mouse IL-6 receptor.
(20) The use according to any of (16) through (19) above wherein the antibody to IL-6 receptor is a recombinant antibody.
(21) The use according to (18) above wherein the monoclonal antibody to human IL-6 receptor is PM-1 antibody.
(22) The use according to (19) above wherein the monoclonal antibody to mouse IL-6 receptor is MR16-1 antibody.
(23) The use according to any of (16) through (22) above wherein the antibody to IL-6 receptor is a chimeric antibody, humanized antibody or human antibody to IL-6 receptor.
(24) The use according to (23) above wherein the humanized antibody to IL-6 receptor is humanized PM-1 antibody.

The present invention can also adopt the forms indicated below.

(1) A treatment method for mesothelioma comprising: administering an interleukin-6 (IL-6) antagonist to a subject requiring that treatment.
(2) The method according to (1) above wherein the mesothelioma is pleural mesothelioma.
(3) The method according to (2) above wherein the pleural mesothelioma is malignant pleural mesothelioma.
(4) The method according to any of (1) through (3) above wherein the IL-6 antagonist is an antibody to IL-6 receptor.
(5) The method according to (4) above wherein the antibody to IL-6 receptor is a monoclonal antibody to IL-6 receptor.
(6) The method according to (4) above wherein the antibody to IL-6 receptor is a monoclonal antibody to human IL-6 receptor.
(7) The method according to (4) above wherein the antibody to IL-6 receptor is a monoclonal antibody to mouse IL-6 receptor.
(8) The method according to any of (4) through (7) above wherein the antibody to IL-6 receptor is a recombinant antibody.
(9) The method according to (6) above wherein the monoclonal antibody to human IL-6 receptor is PM-1 antibody.

(10) The method according to (7) above wherein the monoclonal antibody to mouse IL-6 receptor is MR16-1 antibody.

(11) The method according to any of (4) through (10) above wherein the antibody to IL-6 receptor is a chimeric antibody, humanized antibody or human antibody to IL-6 receptor.

(12) The method according to (11) above wherein the humanized antibody to IL-6 receptor is humanized PM-1 antibody.

(13) A method for inhibiting the growth of mesothelioma cells comprising: administering an interleukin-6 (IL-6) antagonist to a subject requiring that inhibition.

(14) The method according to (13) above in which the mesothelioma is pleural mesothelioma.

(15) The method according to (14) above wherein the pleural mesothelioma is malignant pleural mesothelioma.

(16) The method according to any of (13) through (15) above wherein the IL-6 antagonist is an antibody to IL-6 receptor.

(17) The method according to (16) above wherein the antibody to IL-6 receptor is a monoclonal antibody to IL-6 receptor.

(18) The method according to (16) above wherein the antibody to IL-6 receptor is a monoclonal antibody to human IL-6 receptor.

(19) The method according to (16) above wherein the antibody to IL-6 receptor is a monoclonal antibody to mouse IL-6 receptor.

(20) The method according to any of (16) through (19) above wherein the antibody to IL-6 receptor is a recombinant antibody.

(21) The method according to (18) above wherein the monoclonal antibody to human IL-6 receptor is PM-1 antibody.

(22) The method according to (19) above wherein the monoclonal antibody to mouse IL-6 receptor is MR16-1 antibody.

(23) The method according to any of (16) through (22) above wherein the antibody to IL-6 receptor is a chimeric antibody, humanized antibody or human antibody to IL-6 receptor.

(24) The method according to (23) above wherein the humanized antibody to IL-6 receptor is humanized PM-1 antibody.

BRIEF DESCRIPTION OF THE DRAWINGS

FIG. 3 is a graph that shows the results of Example 3, wherein the production of vascular endothelial growth factor (VEGF) by malignant mesothelioma cell lines H2052 and H2452 is induced by IL-6 and IL-6R.

FIG. 11 is a graph that shows the results of Example 9, wherein promotion of the growth of cell line H2052 by IL-6 and IL-6R is inhibited by MRA.

BEST MODE FOR CARRYING OUT THE INVENTION

Figure 1:
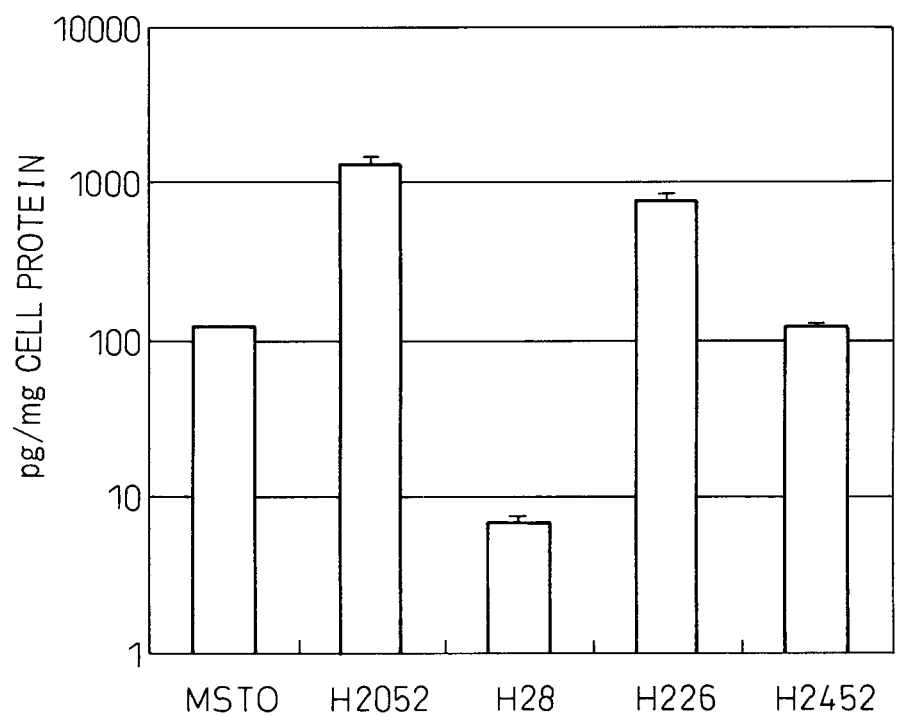
FIG. 1 is a graph that shows the results of Example 1 by indicating the productivities of IL-6 by various malignant mesothelioma cell lines.

IL-6 is a cytokine also referred to as B cell stimulating factor 2 (BSF2) or interferon β2. IL-6 was initially discovered to be differentiation factor involved in activation of B lymphocytic cells (Hirano, T. et al., Nature (1986) 324, 73-76), after which it was determined to be a multifunctional cytokine having effects on the functions of various cells (Akira, S. et al., Adv. In Immunology (1993) 54, 1-78). IL-6 has also been reported to induce maturation of T lymphocytic cells (Lotz, M. et al., J. Exp. Med. (1988) 167, 1253-1258).

IL-6 transmits its biological activity by means of various proteins on cells. One of these is the ligand-binding protein of IL-6 receptors having a molecular weight of about 80 kD (Taga, T. et al., J. Exp. Med. (1987) 166, 967-981; Yamasaki, K. et al., Science (1987) 241, 825-828). In addition to existing in a membrane-bound form that is expressed on the cell membrane by penetrating the cell membrane, IL-6 receptors also exist as soluble IL-6 receptors mainly composed of an extracellular region.

Another of these a membrane protein gp130 having a molecular weight of about 130 kD that is involved in the signal transmission of non-ligand binding. IL-6 and IL-6 receptors form an IL-6/IL-6 receptor complex, and as a result of subsequently binding with gp130, the biological activity of IL-6 is transmitted into cells (Taga, T. et al., Cell (1989) 58, 573-581).

IL-6 antagonists are substances that inhibit the transmission of the biological activity of IL-6. Known examples of these IL-6 antagonists include antibody to IL-6 (anti-IL-6 antibody), antibody to IL-6 receptors (anti-IL-6 receptor antibody), antibody to gp130 (anti-gp130 antibody), IL-6 variant, and IL-6 or IL-6 receptor partial peptide.

There have been several reports regarding anti-IL-6 receptor antibody (Novick, D. et al., Hybridoma (1991) 10, 137-146; Huang, Y. W. et al., Hybridoma (1993) 12, 621-630; International Unexamined Patent Publication No. WO 95-09873; French Unexamined Patent Publication No. FR 2694767, and U.S. Pat. No. 521,628). Humanized PM-1 antibody is known to be obtained by transplanting the complementarity determining region (CDR) of one of these in the form of mouse anti-PM-1 (Hirata, Y. et al., J. Immunol. (1989) 143, 2900-2906) to human antibody (International Unexamined Patent Publication No. WO 92-19759).

The aforementioned IL-6 antagonist is preferably an antibody to IL-6 receptor, and more preferably a monoclonal antibody to human IL-6 receptor or monoclonal antibody to mouse IL-6 receptor. An example of the aforementioned monoclonal antibody to human IL-6 receptor is PM-1 antibody, while an example of monoclonal antibody to mouse IL-6 receptor is MR16-1 antibody. The aforementioned antibody is preferably a chimeric antibody, humanized antibody or human antibody, an example of which is humanized PM-1 antibody.

There are particular limitations on the origin, type or form of the IL-6 antagonist used in the present invention provided it inhibits the growth of mesothelioma cells and is useful as an active ingredient of a mesothelioma therapeutic agent.

IL-6 antagonists are substances that inhibit the biological activity of IL-6 by interrupting signal transmission by IL-6. IL-6 antagonists are preferably substances that have inhibitory action against the binding of IL-6, IL-6 receptor and gp130. Examples of IL-6 antagonists include anti-IL-6 antibody, anti-IL-6 receptor antibody, anti-gp130 antibody, IL-6 variants, soluble IL-6 receptor variants, IL-6 receptor partial peptides and low molecular weight substances demonstrating similar activity.

Anti-IL-6 antibody used in the present invention can be obtained as a polyclonal or monoclonal antibody using known methods. Monoclonal antibody of mammalian origin is particularly preferable for the anti-IL-6 antibody used in the present invention. Examples of monoclonal antibodies of mammalian origin include those produced by hybridomas and those produced by hosts transformed with an expression vector containing antibody gene using genetic engineering techniques. This antibody interrupts the transmission of the biological activity of IL-6 to cells as a result of inhibiting binding of IL-6 to IL-6 receptors by binding with IL-6.

Examples of these antibodies include MH166 (Matsuda, T. et al., Eur. J. Immunol. (1998) 18, 951-956), and SK2 antibody (Sato, K. et al., 21st General Meeting of the Japanese Society for Immunology, Academic Record (1991) 21, 166).

Anti-IL-6 antibody-producing hybridoma can basically be produced in the manner described below using known technology. Namely, this antibody can be produced by using IL-6 as a sensitizing antigen, immunizing with this in accordance with ordinary immunization methods, fusing the resulting immunocytes with known host cells according to ordinary cell fusion methods, and then screening for cells that produce monoclonal antibody according to ordinary screening methods.

More specifically, production of IL-6 antibody should be carried out in the manner described below. Human IL-6 used as sensitizing antigen for acquiring antibody is obtained by using the IL-6 gene/amino acid sequence disclosed in Eur. J. Biochem. (1987) 168, 543-550; J. Immunol. (1988) 140, 1534-1541; or, Agr. Biol. Chem. (1990) 54, 2685-2688.

After inserting the IL-6 gene sequence into a known expression vector system and transforming suitable host cells, the target IL-6 protein is purified by known methods from the host cells or culture supernatant, followed by using this purified IL-6 protein as a sensitizing antigen. In addition, a fused protein consisting of IL-6 protein and another protein may also be used as sensitizing antigen.

The anti-IL-6 receptor antibody used in the present invention can be obtained in the form of a polyclonal antibody or monoclonal antibody using known means. Monoclonal antibody of mammalian origin is particularly preferable for the anti-IL-6 receptor antibody used in the present invention. Examples of monoclonal antibody originating in mammalian cells include those produced by hybridomas and those produced in a host transformed with an expression vector that contains antigen gene by genetic engineering techniques. As a result of this antibody binding to IL-6 receptors, binding of IL-6 to IL-6 receptors is inhibited, thereby interrupting the transmission of the biological activity of IL-6 to cells.

Examples of these antibodies include MR16-1 antibody (Tamura, T. et al., Proc. Natl. Acad. Sci. USA (1993) 90, 11924-11928), PM-1 antibody (Hirata, Y. et al., J. Immunol. (1989) 143, 2900-2906), AUK12-20 antibody, AUK64-7 and AUK146-15 antibody (International Unexamined Patent Publication No. WO 92-19759). Among these, PM-1 antibody is particularly preferable for use as the antibody.

Furthermore, a PM-1 antibody-producing hybridoma cell line has been internationally deposited based on the Budapest Treaty under the designation FERM BP-2998 on Jul. 12, 1989 at the International Patent Organism Depository of the National Institute of Advanced Industrial Science and Technology (Tsukuba Central 6, 1-1-1 Higashi, Tsukuba, Ibaraki, Japan) as PM-1. In addition, an MR16-1 antibody-producing hybridoma cell line has been internationally deposited based on the Budapest Treaty under the designation FERM BP-5875 on Mar. 13, 1997 at the International Patent Organism Depository of the National Institute of Advanced Industrial Science and Technology (Tsukuba Central 6, 1-1-1 Higashi, Tsukuba, Ibaraki, Japan) as Rat-mouse hybridoma MR16-1.

Anti-IL-6 receptor monoclonal antibody-producing hybridoma can basically be produced in the manner described below using known technology. Namely, this hybridoma can be produced by using IL-6 receptor as sensitizing antigen, immunizing with this in accordance with ordinary immunization methods, fusing the resulting immunocytes with known host cells according to ordinary cell fusion methods, and screening for cells that produce monoclonal antibody according to known screening methods.

More specifically, anti-IL-6 receptor antibody should be produced in the manner described below. For example, human IL-6 receptor used as sensitizing antigen for acquisition of antibody is obtained by using the IL-6 receptor gene/amino acid sequence disclosed in European Unexamined Patent Publication No. EP 325474, while mouse IL-6 receptor is obtained by using the IL-6 receptor gene/amino acid sequence disclosed in Japanese Unexamined Patent Publication No. 3-155795.

There are two types of IL-6 receptor protein consisting of that which is expressed on the cell membrane and that which is released from the cell membrane (soluble IL-6 receptor) (Yasukawa, K. et al., J. Biochem. (1990) 108, 673-676). Soluble IL-6 receptor antibody is substantially composed of the extracellular region of IL-6 receptor that binds to the cell membrane, and differs from membrane-bound IL-6 receptor in that it is missing a cell membrane-penetrating region or cell membrane-penetrating region and intracellular region. IL-6 receptor protein may use either IL-6 receptor provided it can be used as sensitizing antigen for producing the anti-IL-6 receptor antibody used in the present invention.

After inserting the gene sequence of IL-6 receptor into a known expression vector system to transform suitable host cells, the target IL-6 receptor is purified by known methods from the host cells or culture supernatant followed by using the purified IL-6 receptor protein as sensitizing antigen. In addition, a fused protein consisting of cells that express IL-6 receptor or IL-6 receptor protein and another protein may also be used as sensitizing antigen.

*Escherichia coli* (*E. coli*) containing plasmid pIBIBSF2R that contains cDNA encoding human IL-6 receptor has been internationally deposited based on the Budapest Treaty under the deposit number FERM BP-2232 on Jan. 9, 1989 at the International Patent Organism Depository of the National Institute of Advanced Industrial Science and Technology (Tsukuba Central 6, 1-1-1 Higashi, Tsukuba, Ibaraki, Japan) as HB101-pIBIBSF2R.

Anti-gp130 antibody used in the present invention can be obtained in the form of polyclonal antibody or monoclonal antibody using known means. Monoclonal antibody of mammalian origin is particularly preferable for the anti-gp130 antibody used in the present invention. Monoclonal antibodies of mammalian origin include those produced by hybridomas and those produced in a host transformed with an expression vector that contains antibody gene by genetic engineering techniques.

This antibody inhibits binding of IL-6/IL-6 receptor complex to gp130 and interrupts the transmission of the biological activity of IL-6 to cells by binding with gp130.

Examples of these antibodies include AM64 antibody (Japanese Unexamined Patent Publication No. 3-219894), 4B11 antibody, 2H4 antibody (U.S. Pat. No. 5,571,513) and B-P8 antibody (Japanese Unexamined Patent Publication No. 8-291199).

Anti-gp130 monoclonal antibody-producing hybridoma can basically be produced in the manner described below using known technology. Namely, this hybridoma can be produced by using gp130 as a sensitizing antigen, immunizing with this in accordance with ordinary immunization methods, fusing the resulting immunocytes with known host cells according to ordinary cell fusion methods, and screening for cells that produce monoclonal antibody according to ordinary screening methods.

More specifically, monoclonal antibody should be produced in the manner described below. For example, gp130 used as sensitizing antigen for acquiring antibody is obtained by using the gp130 gene/amino acid sequence disclosed in European Unexamined Patent Publication No. EP 411946.

After inserting the gene sequence of gp130 into a known expression vector system to transform suitable host cells, the target gp130 protein is purified from the host cells or culture supernatant by known methods, followed by using the purified gp130 receptor protein as sensitizing antigen. In addition, a fused protein consisting of cells expressing gp130 or gp130 protein and another protein may also be used as sensitizing antigen.

Although there are no particular limitations on the mammal immunized with sensitizing antigen, it is preferably selected in consideration of compatibility with the host cells used for cell fusion, typical examples of which include rodents such as mice, rats and hamsters.

Immunization of the animal with sensitizing antigen is carried out in accordance with known methods. As a typical example of such a method, immunization is preferably carried out by injecting sensitizing antigen into the abdominal cavity or beneath the skin of a mammal. More specifically, a suspension of sensitizing antigen diluted to a suitable amount with phosphate-buffered saline (PSB) or physiological saline is mixed with a suitable amount of an ordinary adjuvant such as Freund's complete adjuvant as desired followed by emulsifying and administering several times to the mammal every 4 to 21 days. In addition, a suitable carrier can be used when immunizing with the sensitizing antigen.

After confirming that immunization has been carried out in this manner and the antibody level in serum has risen to a desired level, immunocytes are removed from the mammal and used for cell fusion. Spleen cells are a particularly preferable example of immunocytes used for cell fusion.

Various known cell lines such as P3X6Ag8.653 (Kearney, J. F. et al., J. Immunol. (1979) 123, 1548-1550), P3X63Ag8U.1 (Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415, SP2/0 (Shulman, M. et al., Nature (1978) 276, 269-270), F0 (de St. Groth, S. F. et al., J. Immunol. Methods (1980) 35, 1-21), S194 (Trowbridge, I. S., J. Exp. Med. (1978) 148, 313-323) or R210 (Galfre, G. et al., Nature (1979) 277, 131-133) are already suitably used as mammalian myeloma cells serving as the other host cells fused with the aforementioned immunocytes.

Fusion of the aforementioned immunocytes and myeloma cells can basically be carried out in compliance with known methods such as the method of Milstein, et al. (Kohler, G. and Milstein, C., Methods Enzymol. (1981) 73, 3-46).

More specifically, the aforementioned cell fusion is carried out, for example, in an ordinary nutritive culture liquid in the presence of a cell fusion promoter. Examples of fusion promoters that are used include polyethylene glycol (PEG) and Sendai virus (HVJ), and an assistant such as dimethylsulfoxide can also be added to enhance fusion efficiency as desired.

The ratio of immunocytes and myeloma cells used is preferably 1 to 10 times more immunocytes than myeloma cells. Examples of culture liquids that can be used for the aforementioned cell fusion include RPMI1640 culture liquid preferable for growth of the aforementioned myeloma cells, MEM culture liquid and other ordinary culture liquids used for this type of cell culturing.

Moreover, a serum supplement such as fetal calf serum (FCS) can also be used in combination with the aforementioned culture liquid.

Cell fusion is carried out by thoroughly mixing predetermined amounts of the aforementioned immunocytes and myeloma cells in the aforementioned culture liquid, adding PEG solution, such as PEG solution having an average molecular weight of about 1000 to 6000 and pre-warmed to 37° C., normally at a concentration of 30 to 60% (w/v), and then mixing to form the target fused cells (hybridoma). Continuing, cell fusion agents and so forth that are detrimental to hybridoma development can be removed by repeating the procedure consisting of sequentially adding suitable culture liquid and then centrifuging to remove the supernatant.

The hybridoma is selected by culturing in an ordinary selective culture liquid such as HAT culture liquid (culture liquid containing hypoxanthine, aminopterin and thymidine). Culturing in said HAT culture liquid is continued for a duration, which is normally from several days to several weeks, that is sufficient for destroying those cells other than the target hybridoma (non-fused cells). Next, hybridoma that produces the target antibody is then screened and cloned by carrying out ordinary limiting dilution methods.

In addition to obtaining the aforementioned hybridoma by immunizing animals other than humans with antigen, a desired human antibody having binding activity with a desired antigen or antigen-expressing cells can be obtained by sensitizing human lymphocytes with a desired antigen protein or antigen-expressing cells in vitro, and then fusing the sensitized B lymphocytes with myeloma cells such as U266 (refer to Japanese Examined Patent Publication No. 1-59878). Moreover, a desired human antibody may also be acquired in accordance with the aforementioned method by administering antigen or antigen-expressing cells into a transgenic animal having a repertoire of human antibody genes (refer to International Unexamined Patent Publications Nos. WO 93/12227, WO 92/03918, WO 94/02602, WO 94/25585, WO 96/34096 or WO 96/33735).

Hybridoma that produces monoclonal antibody produced in this manner can be sub-cultured in ordinary culture liquid and stored in liquid nitrogen for a long period of time.

A method in which the hybridoma is cultured in accordance with ordinary methods and obtained in the form of the culture supernatant, or a method in which the hybridoma is grown by administering to a mammal that is compatible therewith followed by obtaining the form of ascites, can be employed to acquire monoclonal antibody from the hybridoma. The former method is suitable for obtaining highly pure antibody, while the latter method is suitable for producing antibody in large volume.

For example, production of anti-IL-6 receptor antibody-producing hybridoma can be carried out according to the method disclosed in Japanese Unexamined Patent Publication No. 3-139293. This can be carried out using a method in which the PM-1-producing hybridoma internationally deposited based on the Budapest Treaty under the designation FERM BP-2998 on Jul. 12, 1989 at the International Patent Organism Depositary of the National Institute of Advanced Industrial Science and Technology (Tsukuba Central 6, 1-1-1 Higashi, Tsukuba, Ibaraki, Japan) is injected into the abdominal cavity of BALB/c mice to obtain ascites followed by purification of PM-1 antibody from the ascites, or a method in which said hybridoma is cultured in a medium such as 10% fetal calf serum, RPMI1640 medium containing 5% BM-Condimed H1 (Boehringer-Mannheim), hybridoma SFM medium (Gibco-BRL) or PFHM-11 medium (Gibco-BRL), followed by purification of PM-1 antibody from the culture supernatant.

Recombinant antibody produced using gene recombination technology by cloning antibody gene from a hybridoma, incorporating in a suitable vector and then inserting into a host can be used as monoclonal antibody in the present invention (refer to, for example, Borrebaeck, C. A. K. and Larrick, J. W., Therapeutic Monoclonal Antibodies, publishing in the United Kingdom by MacMillan Publishers Ltd., 1990).

More specifically, mRNA that encodes antibody variable (V) region is isolated from cells such as a hybridoma that produce the target antibody. Isolation of mRNA is carried out by preparing total RNA according to a known method such as guanidine centrifugation (Chirgwin, J. M. et al., Biochemistry (1979) 18, 5294-5299) or AGPC (Chomczynski, P. et al., Anal. Biochem. (1987) 162, 156-159), and the preparing mRNA using an mRNA Purification Kit (Pharmacia) and so forth. In addition, mRNA can be prepared directly by using the QuickPrep mRNA Purification Kit (Pharmacia).

cDNA of the antibody V region is synthesized from the resulting mRNA using reverse transcriptase. Synthesis of cDNA can be carried out using, for example, the AMV Reverse Transcriptase First-Strand cDNA Synthesis Kit. In addition, The 5'-Ampli Finder Race Kit (Clontech) and 5'-RACE method using PCR (Frohman, M. A. et al., Proc. Natl. Acad. Sci. USA (1988) 85, 8998-9002) can be used to synthesize and amplify the cDNA. The target DNA fragment is purified from the resulting PCR product and coupled with vector DNA. Moreover, a recombinant vector is then produced from this and inserted into $E.$ $coli$ and so forth followed by selecting a colony to prepare the desired recombinant vector. The base sequence of the target DNA is then confirmed by a known method such as the deoxy method.

Once DNA that encodes the V region of the target antibody, this is then coupled with DNA that encodes a desired antibody constant region (C region) followed by incorporation into an expression vector. Alternatively, DNA encoding the V region of the antibody may be incorporated into an expression vector that contains DNA of the antibody C region.

In order to produce antibody used in the present invention, an antibody gene as will be described later is incorporated into an expression vector that expressed under the control of, for example, an enhancer or a promoter. Next, host cells are transformed with this expression vector to allow expression of the antibody.

In the present invention, a gene recombinant antibody that has been artificially altered for the purpose of lowering interspecies antigenicity to humans can be used, examples of which include chimeric antibody, humanized antibody and human antibody. These altered antibodies can be produced using known methods.

Chimeric antibodies are obtained by coupling DNA encoding antibody V region obtained in the manner described above with DNA encoding human antibody C region followed by incorporating the coupled product into an expression vector and producing by inserting into a host (refer to European Unexamined Patent Publication No. EP 125023 or International Unexamined Patent Publication No. WO 92-19759). Chimeric antibody that is useful in the present invention can be obtained by using this known method.

For example, plasmids containing DNA that encode the V regions of the L chain and H chain of chimeric PM-1 antibody have been named pPM-k3 and pPM-h1, respectively, and $Escherichia$ $coli$ retaining these plasmids have been internationally deposited based on the Budapest Treaty under the designation NCIMB40366 and NCIMB40362, respectively, on Feb. 12, 1991 at the National Collections of Industrial and Marine Bacteria Limited (23 St Machar Drive, Aberdeen AB2 1RY, Scotland, Commonwealth of Great Britain and Northern Ireland).

Humanized antibodies, which are also referred to as reshaped antibodies, are obtained by transplanting the complementarity determining region (CDR) of mammals other than humans such as mice to the complementarity determining region of human antibody, and their typical gene recombination techniques are known (refer to European Unexamined Patent Publication No. EP 125023 or International Unexamined Patent Publication No. WO 92-19759).

More specifically, a DNA sequence designed so as to couple CDR of mouse antibody with the framework (FR) region of human antibody is synthesized by PCR from a plurality of oligonucleotides produced so as to have overlapping portions on their ends. The resulting DNA is then coupled with DNA that encodes human antibody C region followed by incorporation into an expression vector and insertion into a host to produce the DNA in that host (refer to European Unexamined Patent Publication No. EU 239400 or International Unexamined Patent Publication No. WO 92-19759).

An FR for which the complementarity determining region forms a satisfactory antigen binding site is selected for the FR of the human antibody coupled by means of CDR. The amino acids of the framework region of the antibody variable region may be substituted so that the complementary determining region of the reconfigured human antibody forms a suitable antigen binding site (Sato, K. et al., Cancer Res. (1993) 53, 851-856).

Human antibody C region is used for chimeric antibody and humanized antibody. An example of a human antibody C region is Cγ, and for example, Cγ1, Cγ2, Cγ3 or Cγ4 can be used. In addition, the human antibody C region may be modified to improve stability of the antibody or its production.

Chimeric antibodies are composed of a variable region of an antibody of mammalian origin other than humans and a C region originating in human antibody, while humanized antibodies are composed of a complementarity determining region of an antibody of mammalian origin other than humans and a framework region and C region originating in human antibody, and since their antigenicity in humans is decreased, they are useful as antibodies used in the present invention.

A preferable specific example of a humanized antibody used in the present invention is humanized PM-1 antibody (refer to International Unexamined Patent Publication No. WO 92-19759).

In addition to the method previously described, another known technology for acquiring human antibody consists of acquiring human antibody by panning using a human antibody library. For example, a phage that binds to an antigen can also be selected by using a variable region of human antibody as a single chain antibody (scFv) and expressing on the surface of a phage using the phage display method. The DNA sequence that encodes the human antibody variable region that binds to the antigen can then be determined by analyzing the genes of the selected phage. Once the DNA sequence of the scFv that binds to the antigen has been identified, an expression vector that is equivalent to that sequence can then be produced to acquire the human antibody. These methods are already commonly known and reference can be made to WO 92/01047, WO 92/20791, WO 93/06213, WO 93/11236, WO 93/19172, WO 95/01438 and WO 95/15388.

Antibody gene constructed in the manner described above can be expressed and acquired by known methods. In the case of mammalian cells, antibody gene can be expressed with DNA or vector that contains said DNA in which a commonly used useful promoter, antibody gene to be expressed, and poly A signal downstream from the 3' side are functionally bound. An example of a promoter/enhancer is human cytomegalovirus immediately early promoter/enhancer.

In addition, examples of other promoters/enhancers that should used to express antibody used in the present invention include virus promoters/enhancers such as those of retrovirus, polyoma virus, adenovirus or Simeon virus 40 (SV40), as well as promoters/enhancers originating in mammalian cells such as human elongation factor 1α (HEF1α).

For example, in the case of using SV40 promoter/enhancer, antibody can be easily expressed in accordance with the method of Mulligan et al. (Mulligan, R. C. et al., Nature (1979) 277, 108-114) or in the case of HEF1α promoter/enhancer, antibody can be easily expressed in accordance with the method of Mizushima et al. (Mizushima, S, and Nagata, S., Nucleic Acids Res. (1990) 18, 5322).

In the case of *Escherichia coli*, antibody can be expressed by functionally binding a commonly used useful promoter, signal sequence for secreting antibody and antibody gene to be expressed. Examples of promoters include lacZ promoter and araB promoter. In the case of using lacZ promoter, antibody should be expressed in accordance with the method of Ward et al. (Ward, E. S. et al., Nature. (1989) 341, 544-546; Ward, E. S. et al., FASEB J. (1992) 6, 2422-2427), or in the case of using araB promoter, antibody should be expressed in accordance with the method of Better et al. (Better, M. et al., Science (1988) 240, 1041-1043).

The pelB signal sequence (Lei, S. P. et al., J. Bacteriol. (1987) 169, 4379-4383) should be used for the signal sequence for antibody secretion in the case of producing in the periplasm of *E. coli*. After separating the antibody produced in the periplasm, the antibody is used after suitably refolding the antibody structure (refer to, for example, WO 96/30394).

Examples of replication sources that can be used include those originating in SV40, polyoma virus, adenovirus or bovine papilloma virus (BPV), and in order to increase the number of gene copies in the host cell system, the expression vector can contain a selection marker such as aminoglycoside phosphotransferase (APH) gene, thymidine kinase (TK) gene, *E. coli* xanthine-guanine phosphoribosyl transferase (Ecogpt) gene or dihydrofolate reductase (dhfr) gene.

Any arbitrary production system can be used to produce antibody used in the present invention. The production system for antibody production may be an in vitro system or an in vivo system. Examples of in vitro production systems include production systems that use eukaryotic cells and a production systems that use prokaryotic cells.

In the case of using eukaryotic cells, the production system may use animal cells, plant cells or fungal cells. Known examples of animal cells include:
(1) mammalian cells such as CHO, COS, myeloma, BHK (baby hamster kidney), HeLa and Vero cells, (2) amphibian cells such as African tree frog follicular cells, and (3) insect cells such as sf9, sf21 and Tn5 cells. Known examples of plant cells include cells originating in *Nicotiana tabacum*, and they should be cultured in calluses. Known examples of fungal cells include yeasts cells such as *Saccharomyces* species including *Saccharomyces cerevisiae*, and molds such as *Aspergillus* species including *Aspergillus niger*.

In the case of using prokaryotic cells, a production system that uses bacterial cells is used. Known examples of bacterial cells include *E. coli* and *Bacillus subtilis*.

Antibody is obtained by inserting the target antibody gene into these cells by transformation, and then culturing the transformed cells in vitro. Culturing is carried out in accordance with known methods. For example, DMEM, MEM, RPMI1640 or IMDM can be used for the culture liquid, and a serum supplement such as fetal calf serum (FCS) can also be used in combination. In addition, antibody may also be produced in vivo by transferring cells into which the antibody gene has been inserted to the abdominal cavity and so forth of an animal.

On the other hand, examples of in vivo production systems include production systems that use animals and production systems that use plants. In the case of using an animal, examples of production systems include those that use mammals or insects.

Examples of mammals that can be used include goats, pigs, sheep, mice and rabbits (Vicki Glaser, SPECTRUM Biotechnology Applications, 1993). Silkworms can be used for the insects. In the case of using plants, tobacco plants can be used, for example.

Antibody gene is inserted into these animals or plants followed by production and recovery of the antibody within the bodies of the animals or plants. For example, an antibody gene is inserted at an intermediate location in a gene that encodes a protein uniquely produced in milk such as goat β casein to prepare in the form of a fused protein. A DNA fragment that contains the fused protein into which the antibody gene has been inserted is then injected into a goat embryo and this embryo is then introduced into a female goat. The desired antibody is then obtained from the milk produced by a transgenic goat or its progeny that is born from the goat that has received the embryo. A suitable hormone may be used in the transgenic goat to increase the amount of milk containing the desired antibody produced from the transgenic goat (Ebert, K. M. et al., Bio/Technology (1994) 12, 699-702).

In addition, in the case of using silkworms, a silkworm is infected with baculovirus into which the target antibody gene has been inserted followed by obtaining the desired antibody from the silkworm body fluid (Maeda, S. et al., Nature (1985) 315, 592-594). Moreover, in the case of using a tobacco plant, the target antibody gene is inserted into a plant expression vector such as pMON 530, after which this vector is inserted into bacteria such as *Agrobacterium tumefaciens*. This bacteria is then used to infect a tobacco plant such as *Nicotiana tabacum* to obtain the desired antibody from the tobacco leaves (Jilian, K.-C. Ma, et al., Eur. J. Immunol. (1994) 24, 131-138).

As has been described above, in the case of producing antibody with an in vitro or in vivo production system, a host may be simultaneously transfected by separately incorporating DNA encoding antibody heavy chain (H chain) or light chain (L chain) in separate expression vectors, or transforming a host by incorporating DNA encoding H chain and L chain in a single expression vector (refer to International Unexamined Patent Publication No. WO 94-11523).

Antibody used in the present invention may be an antibody fragment or modified product thereof provided is can be preferably used in the present invention. Examples of antibody fragments include Fab, F(ab')2, Fv or H chain and single chain Fv (scFv) in which Fv or Fv or H chain and L chain are coupled with a suitable linker.

More specifically, after forming an antibody fragment by treating an antibody with an enzyme such as papain or pepsin, or constructing a gene that encodes these antibody fragments and inserting it into an expression vector, it is expressed in suitable host cells (refer to, for example, Co, M. S. et al., J. Immunol. (1994) 152, 2968-2976; Better, M. & Horwitz, A. H., Methods in Enzymology (1989) 178, 476-496; Plueckthun, A. & Skerra, A., Methods in Enzymology (1989) 178, 476-496; Lamoyi, E., Methods in Enzymology (1989) 121, 652-663; Rousseaux, J. et al., Methods in Enzymology (1989) 121, 663-666; Bird, R. E. et al., TIBTECH (1991) 9, 132-137).

The aforementioned scFv is obtained by coupling antibody H chain V region with L chain V region. In this scFv, the H chain V region and L chain V region are coupled with a linker and preferably a peptide linker (Huston, J. S. et al., Proc. Natl. Acad. Sci. U.S.A. (1988) 85, 5879-5883). The H chain V region and L chain V region in scFv may have for their origins any of the origins described for the aforementioned antibodies. An example of a peptide linker used to couple the V regions is an arbitrary single chain peptide composed of 12-19 amino acid residues.

DNA that encodes scFv is obtained by using DNA that encodes the aforementioned antibody H chain or H chain V region and DNA that encodes L chain or L chain V region as templates, amplifying a DNA portion that encodes a desired amino acid sequence among these sequences by PCR using a primer pair that defines both ends, and then amplifying by combining with a prime pair that defines the DNA that encodes the peptide linker portion as well as both of its ends so that each H chain and L chain is linked.

In addition, once DNA that encodes scFv is produced, expression vectors that contain them as well as hosts that have been transformed by said expression vectors can be obtained in accordance with ordinary methods. In addition, scFv can be obtained in accordance with ordinary methods by using those hosts.

These antibody fragments can be produced from a host by acquiring and expressing their genes in the same manner as previously described. The "antibody" referred to in the present invention includes these antibody fragments.

Antibodies bound with various types of molecules such as polyethylene glycol (PEG) can be used for antibody modified products. The "antibody" referred to in the present invention includes these antibody modified products. These antibody modified products can be obtained by carrying out chemical modification on a resulting antibody. These methods have already been established in this field.

As was previously described, expressed antibody can be separated from inside or outside cells or from a host and purified to uniformity. Separation and purification of antibody used in the present invention can be carried out by affinity chromatography. Examples of columns used for affinity chromatography include a protein A column and protein G column. Examples of carriers used for a protein A column include Hyper D, POROS and Sepharose F.F. Other separation and purification methods used with ordinary proteins may also be used and there are no limitations thereon.

Antibody used in the present invention can be separated and purified by suitably selecting and combining, for example, chromatography other than the aforementioned affinity chromatography, filtration, ultrafiltration, salting out or dialysis. Examples of other types of chromatography include ion exchange chromatography, hydrophobic chromatography and gel filtration. These types of chromatography can be applied to high-performance liquid chromatography (HPLC). In addition, reverse phase HPLC may also be used.

Concentration of antibody obtained as described above can be measured by measurement of optical absorbance, ELISA and so forth. Namely, in the case of measuring optical absorbance, after suitably diluting with PBS(−), optical absorbance at 280 nm is measured followed by calculating concentration based on 1.35 OD representing 1 mg/ml. In addition, measurement of concentration by ELISA can be carried out in the manner described below. Namely, 100 μl of goat anti-human IgG (TAG) diluted to 1 μg/ml with 0.1 M bicarbonate buffer (pH 9.6) are added to a 96-well plate (Nunc) followed by incubating overnight at 4° C. to immobilize the antibody on the plate. After blocking, 100 μl of suitably diluted antibody used in the present invention, sample containing antibody or human IgG standard (Cappel) are added followed by incubating for 1 hour at room temperature.

After washing the plate, 100 µl of 5000×-diluted alkaline phosphatase-labeled anti-human IgG (BIOSOURCE) are added followed by incubating for 1 hour at room temperature. After washing the plate, substrate solution is added followed by incubating and then measuring optical absorbance at 405 nm using a Microplate Reader Model 3550 (BioRad) to calculate the concentration of the target antibody.

IL-6 variant used in the present invention is a substance that has binding activity with IL-6 receptor but does not transmit the biological activity of IL-6. Namely, although IL-6 variant competes with IL-6 for binding with IL-6 receptor, since it does not transmit the biological activity of IL-6, signal transmission by IL-6 is interrupted.

IL-6 variant is produced by introducing a mutation by substituting an amino acid residue in the amino acid sequence of IL-6. Although there are no limitations on the origin of the IL-6 serving as the basis of the IL-6 variant, human IL-6 is preferable in consideration of antigenicity and so forth.

More specifically, this is carried out by predicting the secondary structure of the amino acid sequence of IL-6 using a known molecular modeling program such as WHATIF (Vriend, et al., J. Mol. Graphics. (1990) 8, 52-56), and then evaluating the effects on all of the amino acid residues to be substituted. After determining a suitable substituted amino acid residue, by then using a vector containing a base sequence that encodes human IL-6 gene as a template and introducing a mutation such that the amino acid is substituted by PCR carried out in the normal manner, a gene that encodes IL-6 variant is obtained. This can then be incorporated in a suitable expression vector as necessary to obtain IL-6 variant in compliance with the aforementioned recombinant antibody expression, production and purification methods.

Specific examples of IL-6 variants are disclosed in Brakenhoff et al., J. Biol. Chem. (1994) 269, 86-93, Savino et al., EMBO J. (1994) 13, 1357-1367, WO 96-18648 and WO 96-17869.

IL-6 partial peptide or IL-6 receptor partial peptide used in the present invention is a substance that has binding activity with IL-6 receptor or IL-6, respectively, and does not transmit the biological activity of IL-6. Namely, IL-6 partial peptide or IL-6 receptor partial peptide specifically inhibit binding of IL-6 to IL-6 receptor by capturing IL-6 receptor or IL-6 by binding thereto. As a result, signal transmission by IL-6 is interrupted since the biological activity of IL-6 is not transmitted.

IL-6 partial peptide or IL-6 receptor partial peptide is a peptide that is composed of an amino acid sequence of a portion or entirety of the region involved in binding between IL-6 and IL-6 receptor in the amino acid sequence of IL-6 or IL-6 receptor. Such a peptide is normally composed of 10 to 80, preferably 20 to 50 and more preferably 20 to 40 amino acid residues.

IL-6 partial peptide of IL-6 receptor partial peptide can be produced by a method in which the region involved in binding between IL-6 and IL-6 receptor is identified in the amino acid sequence of IL-6 or IL-6 receptor, and a portion or all of that amino acid sequence is normally known, examples of which include genetic engineering techniques and peptide synthesis methods.

IL-6 partial peptide or IL-6 receptor partial peptide can be produced using genetic engineering techniques by incorporating DNA that encodes a desired peptide in an expression vector and obtaining the desired peptide in compliance with the aforementioned recombinant antibody expression, production and purification methods.

IL-6 partial peptide or IL-6 receptor partial peptide can be produced using peptide synthesis methods by using a method normally used in peptide synthesis, such as a solid phase synthesis method or liquid phase synthesis method.

More specifically, this should be carried out according to the method described in Zokuiyakuhin-no-Kaihatsu, Vol. 14, Peptide Synthesis, N. Yajima, ed., Hirokawa Shoten Publishing (1991). In the case of solid phase synthesis, a method is used in which, for example, a peptide chain is elongated by alternately repeating a reaction in which an amino acid corresponding to the C terminal of the peptide to be synthesized is bound to a support that is insoluble in organic solvent, and amino acids in which the α-amino groups and side chain functional groups are protected with suitable protecting groups are sequentially bound in order from the C terminal to the N terminal, and a reaction in which said protecting groups of α-amino groups of amino acids or peptide bound to the resin are eliminated. Solid phase peptide synthesis methods are broadly divided into the Boc method and Fmoc method depending on the type of protecting groups used.

After synthesizing the target peptide in this manner, a de-protecting reaction and reaction for severing the peptide chain from the support are carried out. In the reaction for severing the peptide chain, hydrogen fluoride or trifluoromethane sulfonic acid are normally used in the Boc method, while TFA is normally used in the Fmoc method. In the Boc method, for example, the aforementioned protected peptide resin is treated in hydrogen fluoride in the presence of anisole. Next, the protecting groups are eliminated and the peptide is severed from the support followed by recovery of the peptide. A crude peptide is then obtained by freeze-drying the product. On the other hand, in the Fmoc method, for example, a de-protecting reaction and reaction for severing the peptide chain from the support can be carried out using the same procedure as described above in TFA.

The resulting crude peptide can be separated and purified by applying to HPLC. Elution should be carried out under the optimum conditions using a water-acetonitrile-based solvent normally used for purification of protein. The fraction corresponding to the peak of the resulting chromatography profile is then separated and freeze-dried. The peptide fraction purified in this manner is then identified by molecular weight analysis using mass spectrometry, amino acid composition analysis or amino acid sequence analysis.

Specific examples of IL-6 partial peptides and IL-6 receptor partial peptides are disclosed in Japanese Unexamined Patent Publication No. 2-188600, Japanese Unexamined Patent Publication No. 7-324097, Japanese Unexamined Patent Publication No. 8-311098 and U.S. Pat. No. 5,210,075.

IL-6 signal transmission inhibitory activity of IL-6 antagonist used in the present invention can be evaluated by normally used methods. More specifically, IL-6-dependent human myeloma line (S6B45, KPMM2), human Lennert's T lymphoma cell line KT3 or IL-6-dependent cell line MH60 or BSF2 is cultured followed by the addition of IL-6 while simultaneously in the presence of IL-6 antagonist and measurement of the uptake of $^3$H-thymidine by IL-6-dependent cells.

In addition, $^{125}$I-labeled IL-6 bound to IL-6 receptor expressing cells is measured by culturing IL-6 receptor expressing cells in the form of U266 cells followed by the addition of $^{125}$I-labeled IL-6 and the simultaneous addition of IL-6 antagonist. In the aforementioned assay system, a negative control group that does not contain IL-6 antagonist is provided in addition to the group in which IL-6 antagonist is present, and comparison of the results obtained from the two groups makes it possible to evaluate the IL-6 inhibitory activity of the IL-6 antagonist.

As will be indicated in the examples to be described later, since growth inhibitory effects on mesothelioma cells have been observed for anti-IL-6 receptor antibody, anti-IL-6 receptor antibody and other IL-6 antagonists were suggested as being useful as therapeutic agents for mesothelioma.

The treatment target in the present invention is a mammal. The mammal of the treatment target is preferably a human.

The mesothelioma therapeutic agent or mesothelioma cell growth inhibitor of the present invention can be administered systemically or locally either orally or parenterally. For example, intravenous infusion or other form of intravenous injection, intramuscular injection, intrathoracic injection, intraperitoneal injection, subcutaneous injection, suppositories, enema or oral enteric-coated pills and so forth can be selected, and the administration method can be suitably selected according to the age and symptoms of the patient. The effective dose is selected within the range of 0.01 mg to 100 mg per kilogram of body weight per administration. Alternatively, a dose of 1 to 1000 mg, and preferably 5 to 50 mg, can be selected per patient.

The preferable dose and administration method in the case of anti-IL-6 receptor antibody, for example, is such that the amount of free antibody present in the blood is the effective dose, a specific example of which is a method by which it is administered using a method such as intravenous drip or other form of intravenous injection or subcutaneous injection and so forth according to an administration schedule such as twice a week, once a week, once every two weeks or once every four weeks in a single administration or divided among several administrations at a dose of 0.5 mg to 40 mg, and preferably 1 mg to 20 mg, per month (4 weeks) per 1 kilogram of body weight. The administration schedule can be adjusted such as by lengthening the administration interval from twice per week or once per week to once every two weeks, once every three weeks or once every four weeks while observing the patient's condition and trends in blood test values.

The mesothelioma therapeutic agent or mesothelioma cell growth inhibitor of the present invention may contain a pharmaceutically acceptable carrier or additive depending on the administration route. Examples of such carriers and additives include water, pharmaceutically acceptable organic solvents, collagen, polyvinyl alcohol, polyvinyl pyrrolidone, carboxyvinyl polymer, sodium carboxymethyl cellulose, sodium polyacrylate, sodium arginate, water-soluble dextran, sodium carboxymethyl starch, pectin, methyl cellulose, ethyl cellulose, xanthan gum, gum Arabic, casein, gelatin, agar, diglycerin, propylene glycol, polyethylene glycol, Vaseline, paraffin, stearyl alcohol, stearic acid, human serum albumin (HSA), mannitol, sorbitol, lactose and surfactants acceptable for use as pharmaceutical additives. Although additives used are selected are suitably selected or combined from the aforementioned additives according to the drug form, they are not limited to those indicated above.

EXAMPLES

Although the following provides a detailed explanation of the present invention through its examples and reference examples, the present invention is not limited thereto.

Example 1

Production of IL-6 by Malignant Mesothelioma Cell Lines

Culturing of malignant mesothelioma cell lines MSTO, H2052, H28, H226 and H2452 was started at a cell concentration of $5 \times 10^4$/well in a 24-well plate containing culture liquid (RPMI containing 10% fetal calf serum (FCS)), the cell culture liquid was replaced on the following day, after which the cells were cultured for additional 3 days followed by measuring the concentrations of IL-6 in the culture supernatant using a fully automated chemiluminescent enzyme immunoassay system (Fujirebio, Lumipulse) and correcting for the amount of cellular protein. Those results are shown in FIG. 1. The experiment was repeated three times. Although cell line H28 did not produce IL-6, the other four lines produced IL-6. Cell lines H2052 and H226 produced particularly high levels of IL-6.

Example 2

Expression of IL-6R in Malignant Mesothelioma Cell Lines

Figure 2:
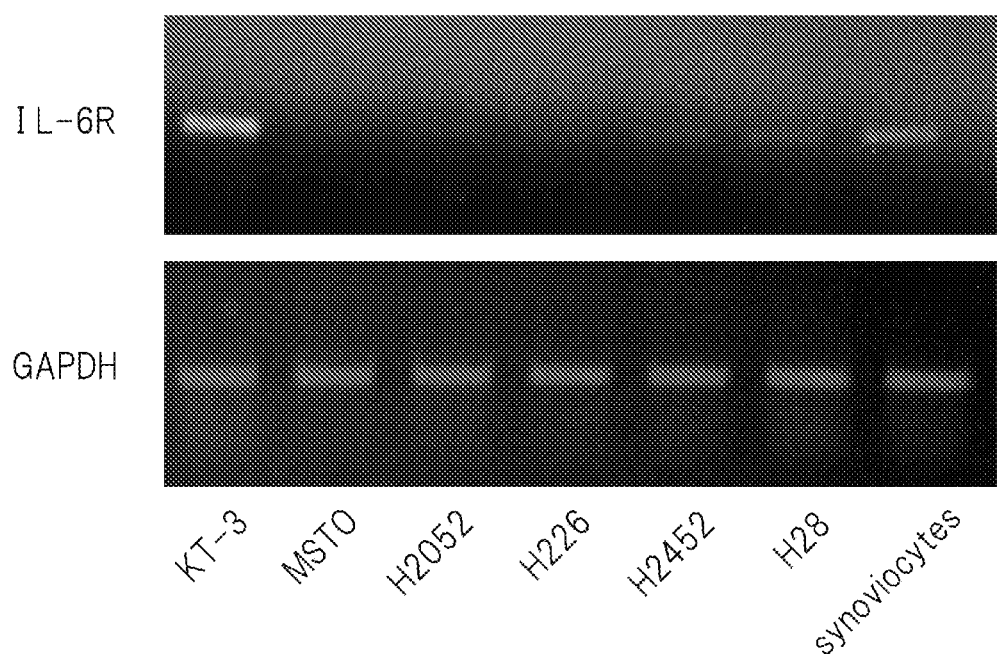
FIG. 2 is a graph that shows the results of Example 2 by indicating the productivities (lack thereof) of IL-6 receptor (IL-6R) by various malignant mesothelioma cell lines. Furthermore, GAPDH indicates the amount of mRNA of GAPDH (glyceraldehyde-3-phosphate dehydrogenase) used as an internal control.

The expression levels of IL-6 receptor were measured for five malignant mesothelioma cell lines at the mRNA level. KT-3 cells were used for the positive control, and synoviocytes were used for the negative control. These cells were cultured for 48 hours in RPMI containing 10% FCS, and mRNA that encodes IL-6 receptor IL-6R) in the cells was measured by reverse-transcribed PCR (RTPCR) using the GeneAmp PCR System (Applied Biosystems) for the detection device. Those results are shown in FIG. 2. FIG. 2 (bottom) indicates the amount of mRNA of the GAPDH (glyceraldehyde-3-phosphate dehydrogenase) used for the internal control.

According to these results, malignant mesothelioma cells are believed to express hardly any IL-6 receptor. Since the pleural fluid in cases of malignant pleural mesothelioma consists of bloody pleural fluid, soluble IL-6 receptor is surmised to be present in large amounts, and this is believed to be involved in transmission of IL-6 irritation.

Example 3

Induction of VEGF Production by IL-6 Stimulation (1)

Tumor cells of malignant mesothelioma cell lines H2052 and H2452 were cultured in three series in 24-well plates at an initial cell concentration of $5 \times 10^4$/well in RPMI1640 medium. On the following day, the cell culture liquid was replaced followed by commencement of stimulation by (1) recombinant IL-6 (10 ng/ml), (2) recombinant IL-6 (10 ng/ml)+recombinant soluble IL-6R (100 ng/ml), and (3) inhibition by the anti-IL-6 receptor antibody, humanized PM-1 antibody (refer to WO 92/19759) (25 µg/ml) (RPMI was used for the medium control). After culturing for an additional 3 days, the concentrations of vascular endothelial growth factor (VEGF) in the culture supernatants were measured using the Quantikine Human VEGF Immunoassay Kit (R & D Systems) and corrected for the amount of cellular protein.

Those results are shown in FIG. 3. As is clear from these graphs, production of VEGF was inducted by IL-6 stimulation in both cell lines H2052 and H2452.

Example 4

Induction of VEGF Production by IL-6 Stimulation (2)

Figure 4:
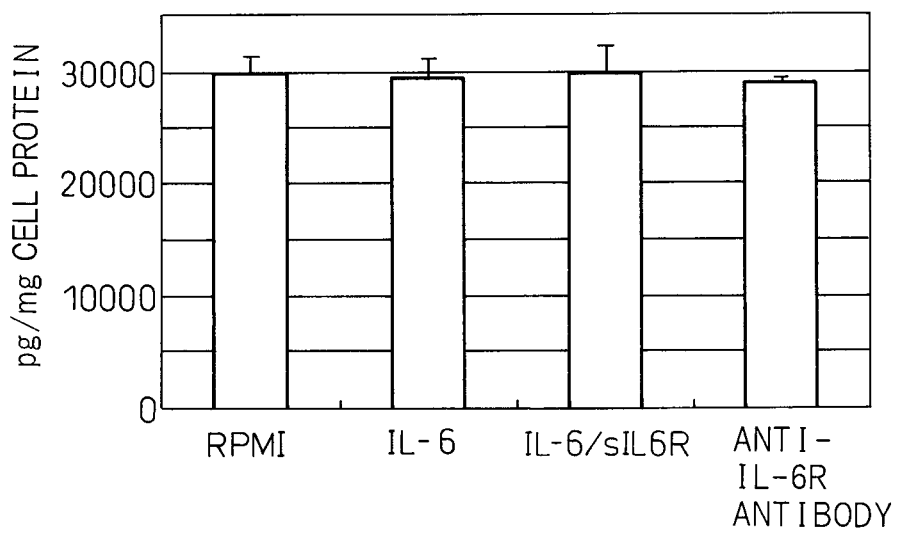
FIG. 4 is a graph that shows the results of Example 4 in which a similar experiment to Example 3 was conducted for malignant mesothelioma cell line H28 by indicating that this cell line produces vascular endothelial growth factor (VEGF) without requiring induction by IL-6/IL-6R.

The experiment of Example 3 was repeated using malignant mesothelioma cell line H28. Those results are shown in FIG. 4. As is clear from these results, although cell line H28 produces high levels of VEGF, it did not respond to stimulation by IL-6.

Example 5

Phosphorylation of STAT3 by IL-6 Stimulation

Cell line H2025, in which production of VEGF is induced by IL-6, and cell line H28, in which production of VEGF is not induced by IL-6, were incubated in the presence of recombinant IL-6 (10 ng/ml) and soluble recombinant IL-6 receptor (100 ng/ml) together with signal transducer and activator of transcription 3 (STAT3) followed by analysis of the phosphorylation from STAT3 to p-STAT3 in hour 0, hour 0.5 and hour 1 of incubation by Western blotting. Those results are shown in FIG. 5.

Figure 5:
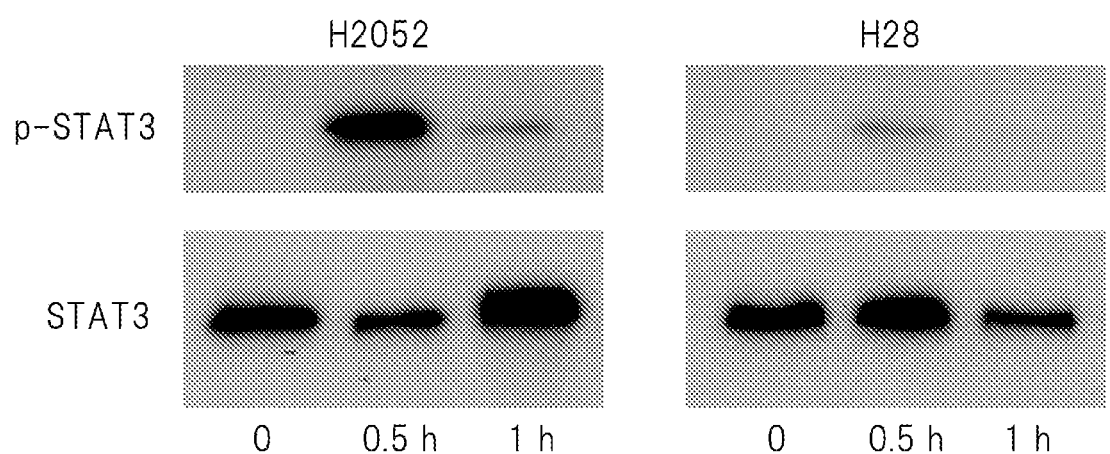
FIG. 5 is a graph that shows the results of Example 5, wherein in contrast to phosphorylation of STAT3 due to stimulation by IL-6 being promoted in cell line H2025, in which production of VEGF is induced by IL-6, phosphorylation of STAT3 due to stimulation by IL-6 is not promoted in cell line H28, in which production of VEGF is not induced by IL-6.

As is clear from FIG. 5, prominent phosphorylation of STAT3 was observed for cell line H2052 at 30 minutes after IL-6 stimulation. In contrast, only slight phosphorylation of STAT3 was observed in response to IL-6 stimulation for cell line H28. Furthermore, p-STAT3 in FIG. 5 indicates phosphorylated STAT3, while STAT3 indicates the sum of phosphorylated and non-phosphorylated STAT3.

Example 6

Induction of SOCS3 by IL-6 Stimulation

Cell line H2025, in which production of VEGF is induced by IL-6, and cell line H28, in which production of VEGF is not induced by IL-6, were stimulated by incubating in the presence of recombinant IL-6 (10 ng/ml) and soluble recombinant IL-6 receptor (100 ng/ml) followed by measuring the expression levels of induced suppressor of cytokine signaling 3 (SOCS3) and glyceraldehyde-3-phosphate dehydrogenase (GAPDH) by measuring the levels of mRNA that encode them following RT-PCR amplification in hour 0, hour 2 and hour 4 of incubation. Those results are shown in FIG. 6.

Figure 6:
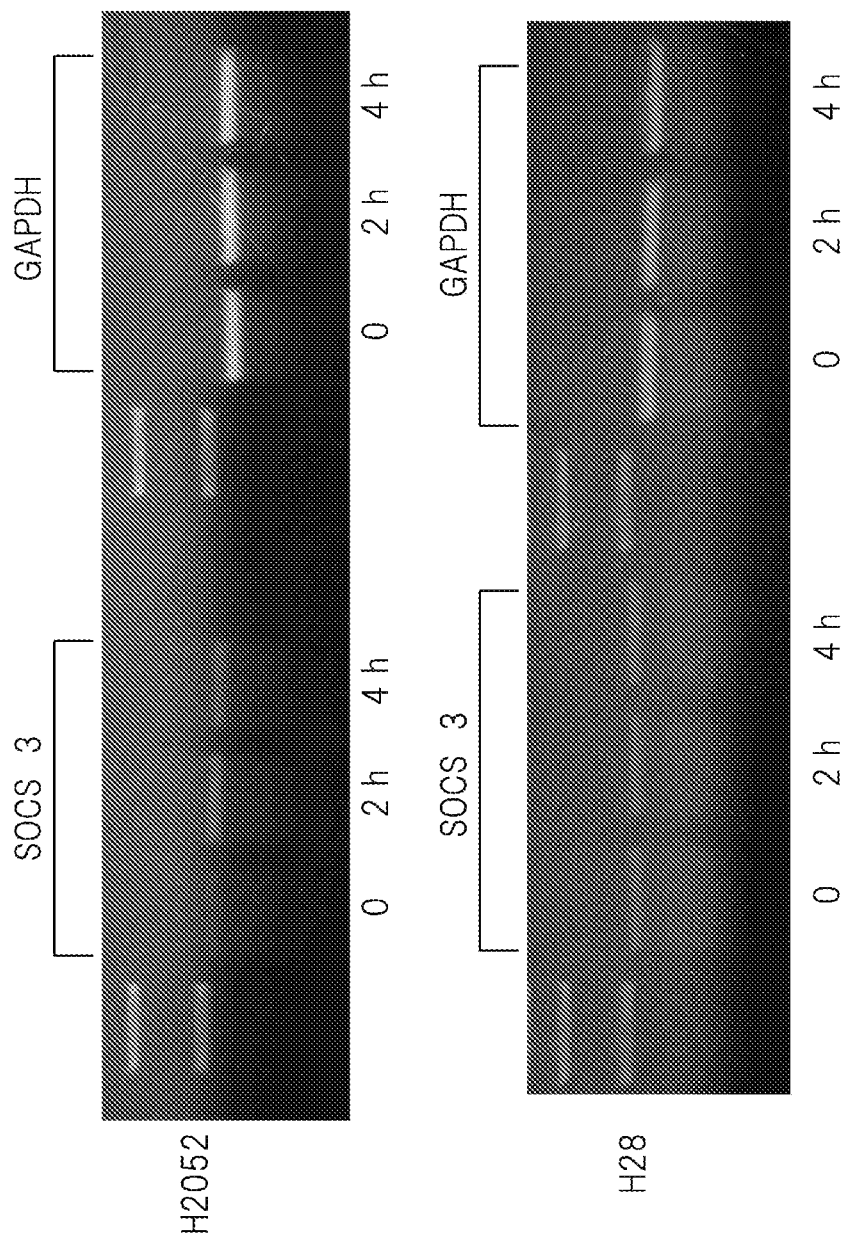
FIG. 6 is a graph that shows the results of Example 6, wherein in contrast to expression of SOCS3 due to stimulation by IL-6 and IL-6R being induced in cell line H2025, in which production of VEGF is induced by IL-6, SOCS3 is non-inductively expressed in cell line H28, in which production of VEGF is not induced by IL-6.

As is clear from FIG. 6, induction of SOCS3 mRNA was observed 2 hours after IL-6 stimulation in cell line H2052. Continuously high expression of SOCS3 was observed in cell line H28.

Example 7

VEGF Promoter Assay

Figure 7:
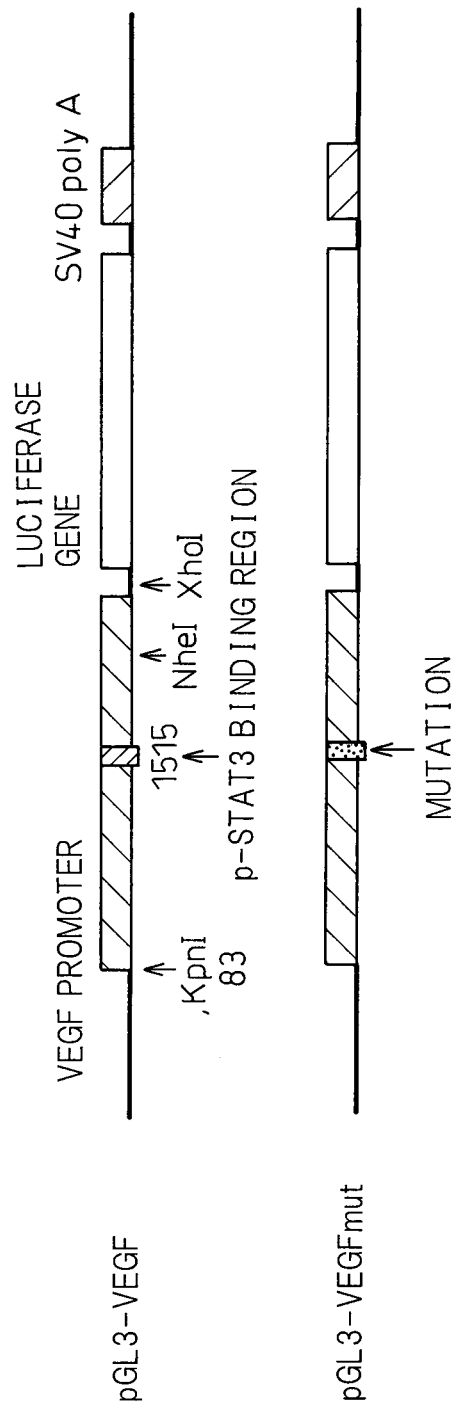
FIG. 7 is a drawing showing the structure of a promoter of plasmids pGL3-VEGF and pGL3-VEGFmut along with its vicinity used in Example 7.

A plasmid pGL3-VEGF, which controls the expression of luciferase gene by VEGF promoter, and a plasmid pGL3-VEGFmut, which controls the expression of luciferase gene by a mutated VEGF promoter, were produced (FIG. 7).

50,000H2052 cells each were transfected with 1 μg of pGL3-VEGF or pGL3-VEGFmut, and the transfected cells were stimulated with recombinant IL-6 (10 ng/ml) and recombinant soluble IL-6 receptor (100 ng/ml). After stimulating for 2 days, the luciferase activity induced from the VEGF promoter and mutated VEGF promoter was examined. Those results are shown in FIG. 8.

Figure 8:
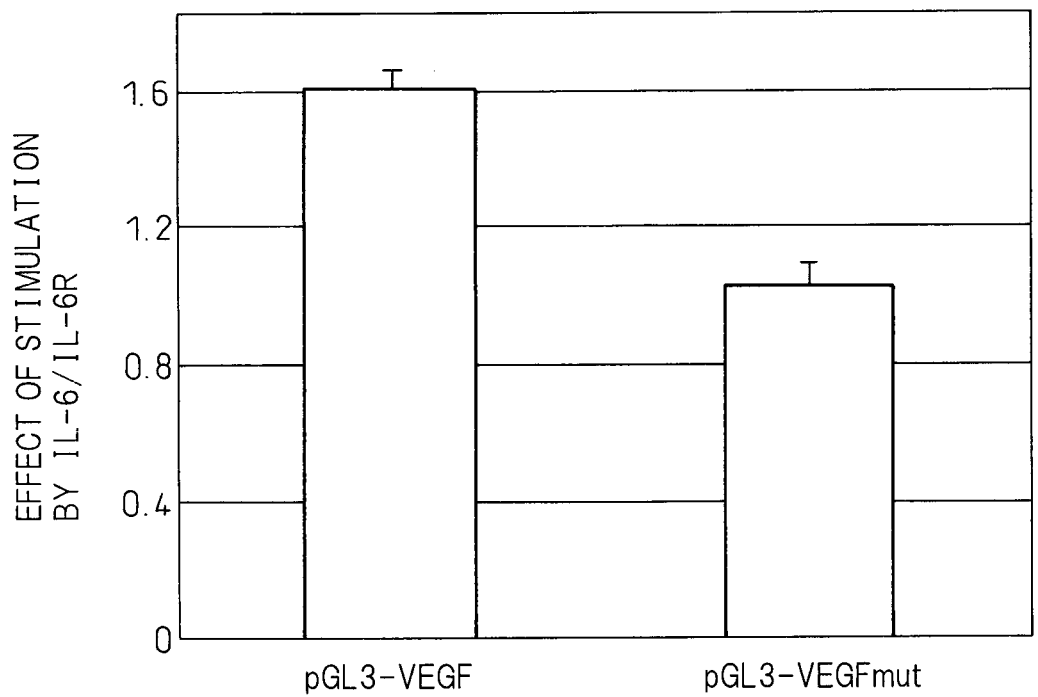
FIG. 8 is a graph that shows the results of Example 7, wherein in a system in which VEGF promoter is coupled to luciferase reporter gene, in the case of altering the p-STAT3 binding site within the VEGF promoter, activation of the VEGF promoter by IL-6 does not occur.
Figure 9:
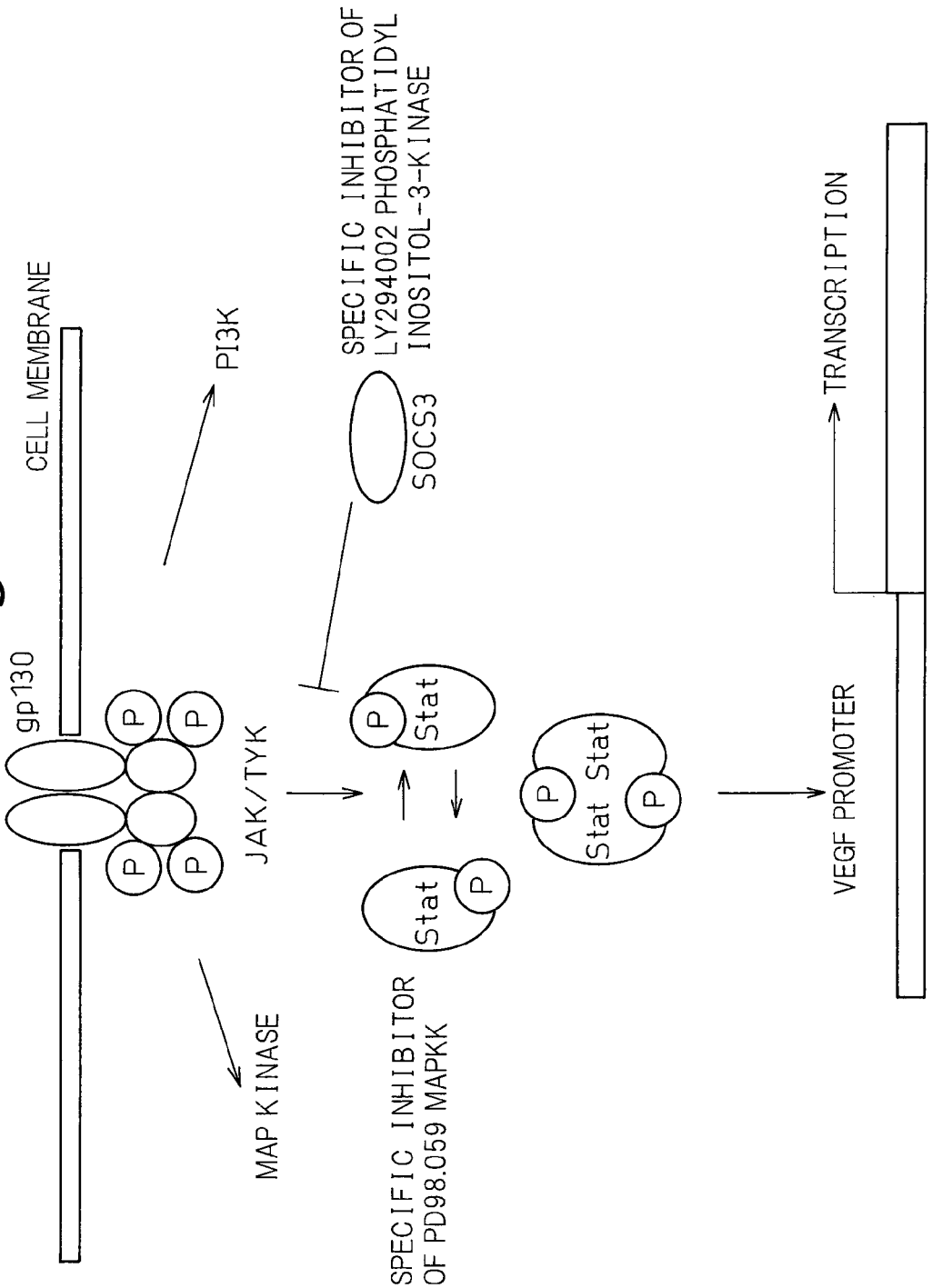
FIG. 9 is a schematic drawing showing the mechanism of induction of VEGF promoter (production of VEGF) due to stimulation by IL-6 in cell line H2052 as predicted from the results of Examples 5 through 7.

As is clear from FIG. 8, in the case of having removed the phosphorylated STAT3 binding site from the VEGF promoter, activation of the VEGF promoter due to IL-6 stimulation was no longer observed. Based on the results of the aforementioned Examples 5, 6 and 7, increased production of VEGF due to IL-6 stimulation in cell line H2052 was believed to be mediated by a JAK-STAT system. This predicted system is shown in FIG. 9.

Example 8

Figure 10:
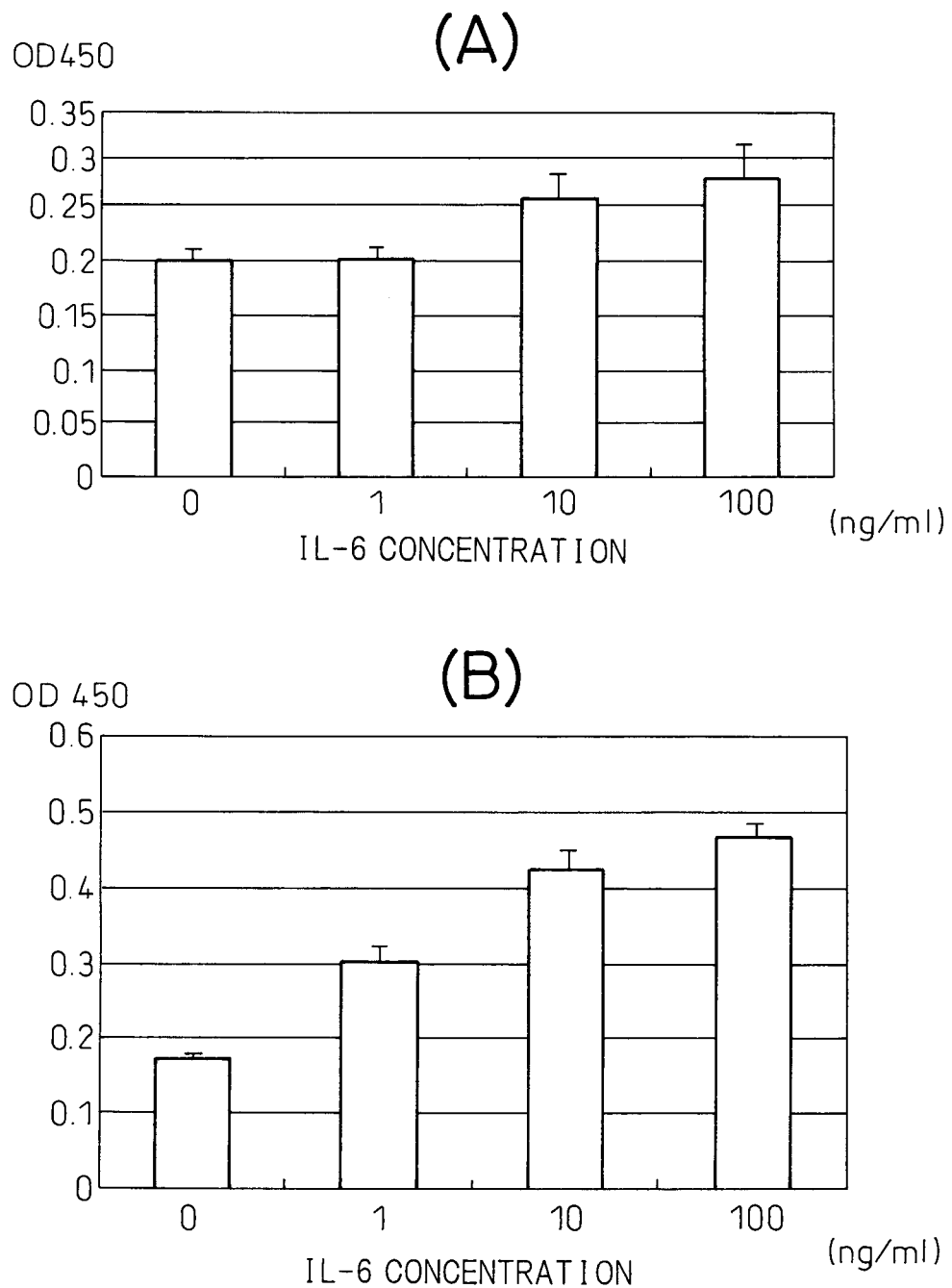
FIG. 10 is a graph that shows the results of Example 8, wherein the growth of cell line H2052 increases IL-6 concentration-dependently in the presence of IL-6R.
Figure 13:
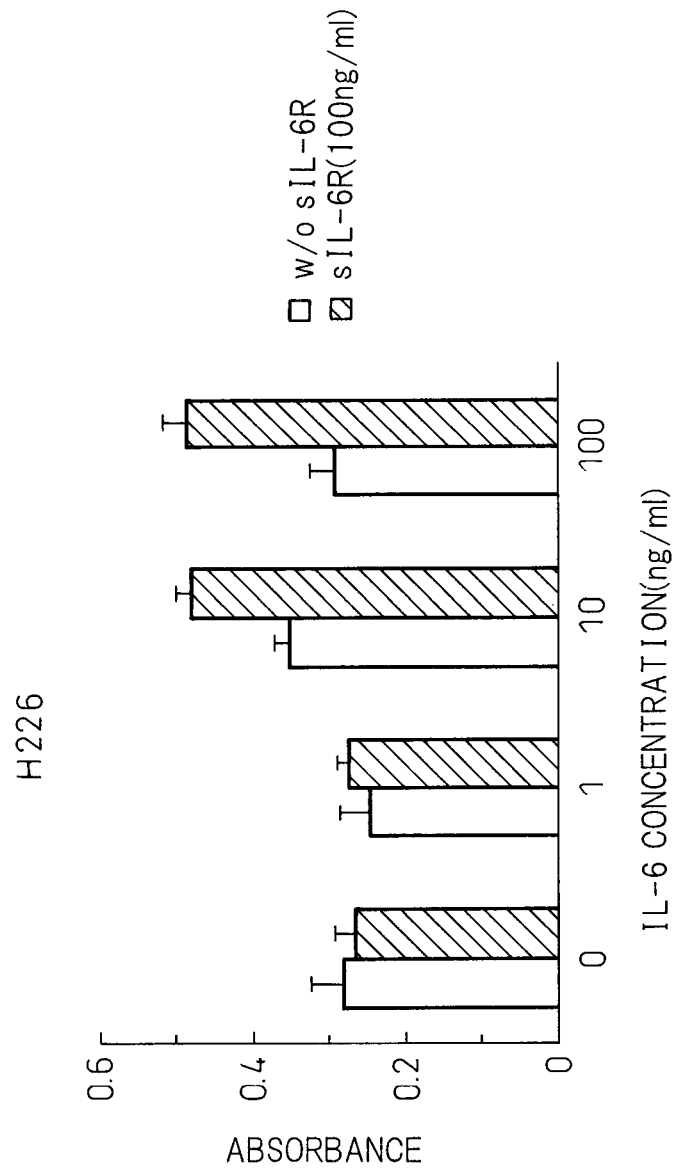
FIG. 13 is a graph that shows the results of Experiment 8 by indicating that the growth of cell line H226 increases IL-6 concentration-dependently in the presence of IL-6R.

Growth Promotion of H2052 and H226 by Addition of IL-6 and Soluble IL-6 Receptor Cell line H2052 cells were disseminated in a 96-well plate containing RPMI medium containing 10% FCS at 500 cells/well followed by culturing in five series for 6 to 7 days in the presence or absence of recombinant soluble IL-6 receptor at 100 ng/ml and in the presence of various concentrations (0, 1, 10 or 100 ng/ml) of IL-6. Those results are shown in FIG. 10 and FIG. 13. As is clear from these graphs, cell line H2052 and cell line H226 grow IL-6 concentration-dependently in the presence of recombinant soluble IL-6 receptor (100 ng/ml).

Example 9

Inhibition of Growth Promotion of H2052 Cells Due to Addition of IL-6 and IL-6R by Antibody to IL-6R (Anti-IL-6R Antibody)

In order to determine whether or not growth promotion of H2052 cells by IL-6 and IL-6 receptor is inhibited by anti-IL-6R antibody, H2052 cells were disseminated in a 96-well plate containing RPMI medium containing 10% FCS at 500 cells/well followed by culturing in three series for 7 days in the presence of recombinant soluble IL-6 at 10 ng/ml and recombinant soluble IL-6 receptor at 100 ng/ml and in the presence of various concentrations (0.1 or 25 μg/ml) of humanized PM-1 antibody. Following culturing, the amount of growth of H2052 cells (OD 450) was measured by MTS assay. Those results are shown in FIG. 11. As a result, anti-IL-6 antibody was determined to inhibit growth concentration-dependently. On the other hand, inhibitory effects were not observed in the case of adding human IgG1 instead of MRA at the same concentration as a control.

Example 10

Figure 12:
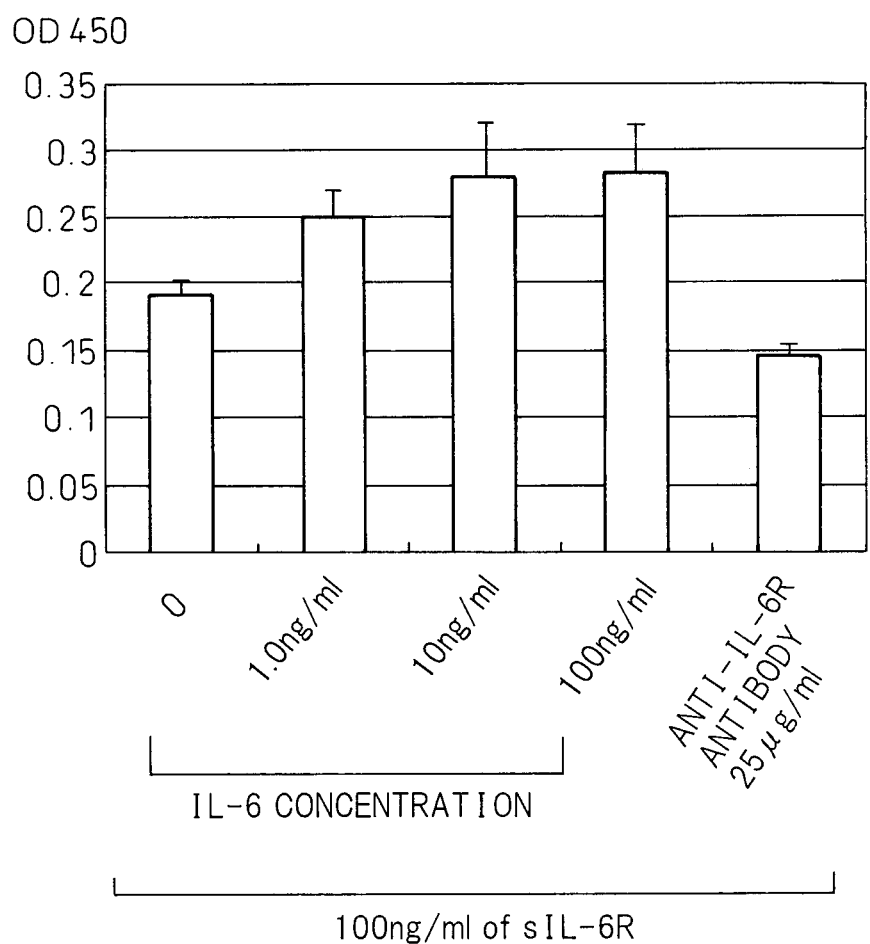
FIG. 12 is a graph that shows the results of Example 10, wherein the growth of cell line H226 increases IL-6 concentration-dependently in the presence of IL-6R, and that MRA demonstrates inhibitory effects on that growth.

Growth Promotion of H226 Cells by Addition of IL-6 and Soluble IL-6 Receptor and Inhibition by Anti-IL-6R Antibody Cell line H226 cells were disseminated in a 96-well plate containing RPMI medium containing 10% FCS at a concentration of 500 cells/well followed by culturing in three series for 7 days in the presence of recombinant soluble IL-6 receptor at 100 ng/ml and in the presence of various concentrations (0, 1, 10 or 100 ng/ml) of IL-6. Those results are shown in FIG. 12. As is clear from the graph, H226 cells that produce high levels of IL-6 grew IL-6 concentration-dependently in the presence of recombinant soluble IL-6 receptor (100 ng/ml) while their growth was inhibited by anti-IL-6R antibody in the same manner as H2052 cells producing high levels of IL-6.

Example 11

Figure 14:
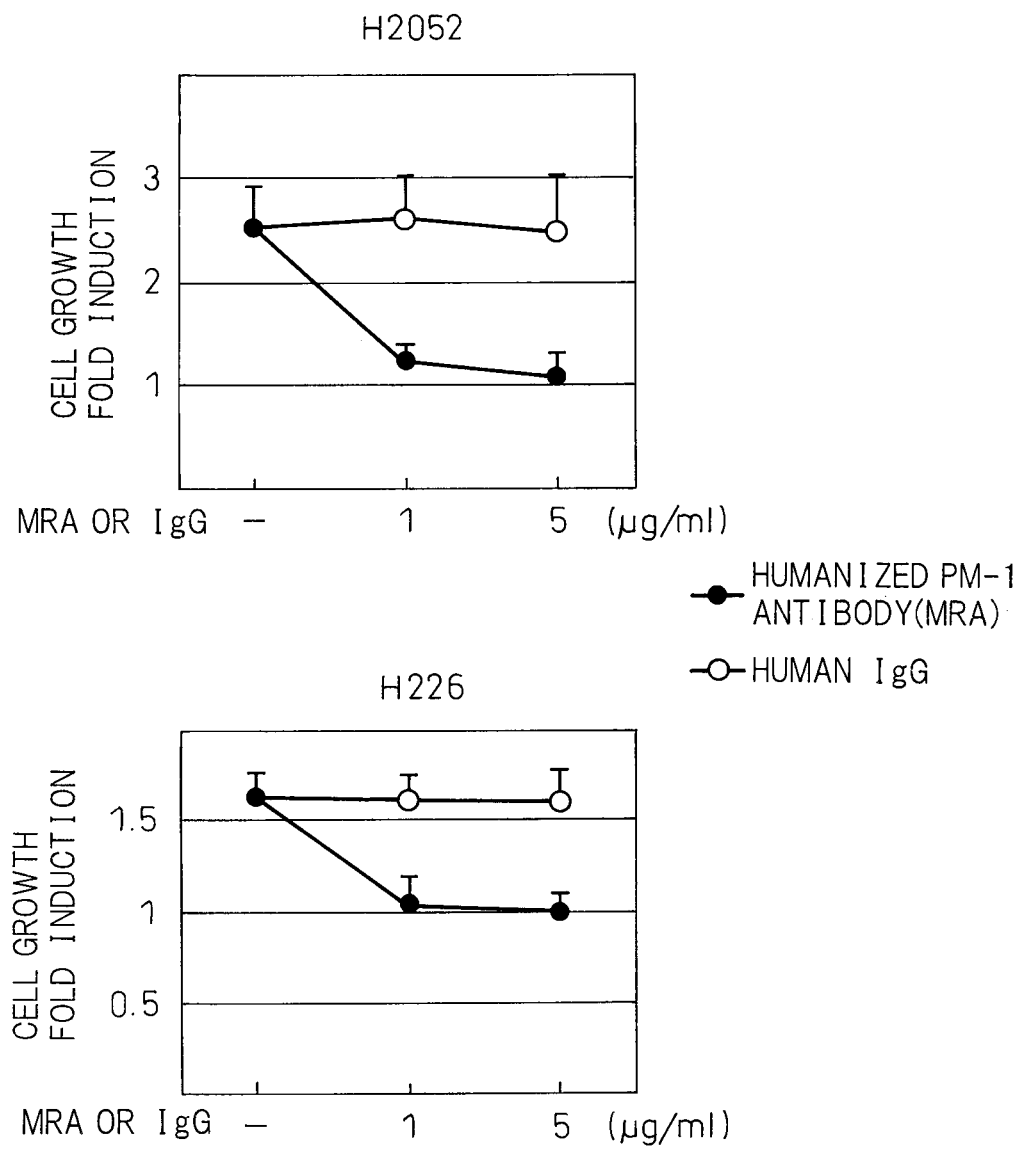
FIG. 14 is a graph that shows the results of Example 11, wherein growth promotion of malignant mesothelioma cell lines H2052 and H226 by IL-6 and soluble IL-6 receptor is inhibited by humanized PM-1 antibody.

Inhibition of Growth Promotion of Cell Line H2052 and Cell Line H226 Induced by Addition of IL-6 and Soluble IL-6 Receptor by Anti-IL-6 Receptor Antibody Cells of cell line H2052 and cell line H225 were disseminated in a 96-well plate at 200 cells/well in RPMI medium containing 10% FCS followed by culturing in five series for 6 days in the presence of IL-6 (10 ng/ml) and soluble IL-6 receptor (100 ng/ml) and in the presence of various concentrations (0, 1 µg/ml, 5 µg/ml) of humanized PM-1 antibody. After culturing, the cell growth rates of cell line H2052 and cell line H226 were measured by MTS assay. The cell growth rates indicated how many times cell growth increased as compared with the absence of addition of IL-6/sIL-6R. Those results are shown in FIG. 14. As a result, anti-IL-6 receptor antibody completely inhibited the growth promoting action induced by addition of IL-6/sIL-6R in cell line H2052 and cell line H226. On the other hand, growth inhibitory effects were not observed in the case of adding the same concentrations of human IgG1 (Sigma) as a control instead of anti-IL-6 receptor antibody.

Example 12

Figure 15:
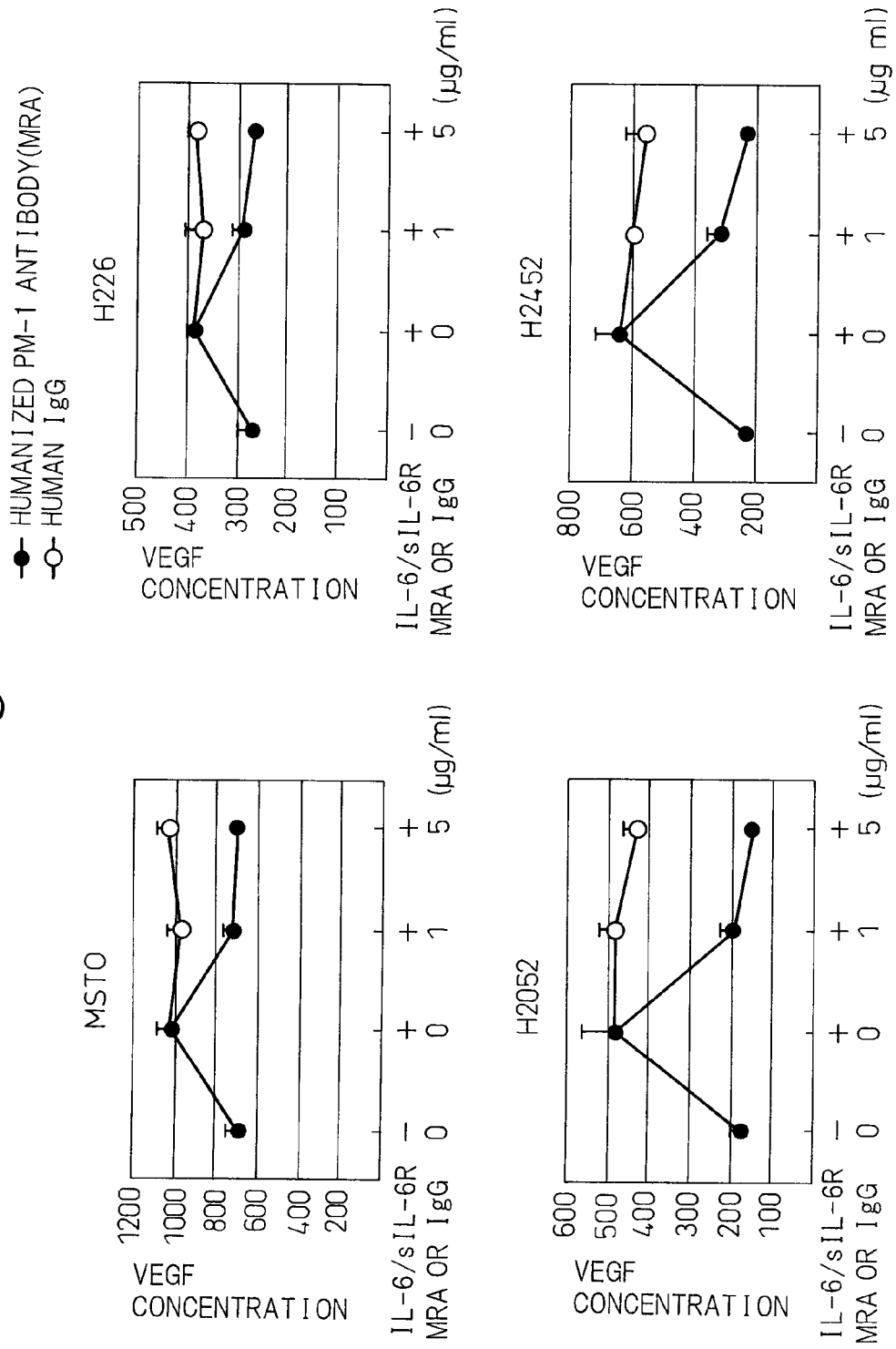
FIG. 15 is a graph that shows the results of Example 12, wherein induction of VEGF production by IL-6 stimulation in the malignant mesothelioma cell lines MSTO, H226, H2052 and H2452 is inhibited by humanized PM-1 antibody.

Inhibition of Induction of VEGF Production Induced by IL-6 Stimulation by Anti-IL-6 Receptor Antibody A study was made of inhibition of the induction of VEGF production induced by IL-6 stimulation in malignant mesothelioma cell lines MSTO, H226, H2052 and H2452 by anti-IL-6 receptor antibody under the same conditions as Example 3 with the exception of the concentrations of the humanized PM-1 antibody (0.1 µg/ml, 5 µg/ml). Those results are shown in FIG. 15. As a result, anti-IL-6 receptor antibody completely inhibited induction of VEGF production induced by IL-6/sIL-6R stimulation. On the other hand, inhibitory action on induction of VEGF production was not observed in the case of adding the same concentrations of human IgG1 (Sigma) as a control instead of anti-IL-6 receptor antibody.

Example 13

Inhibition of STAT3 Phosphorylation by Anti-IL-6 Receptor Antibody

Figure 16:
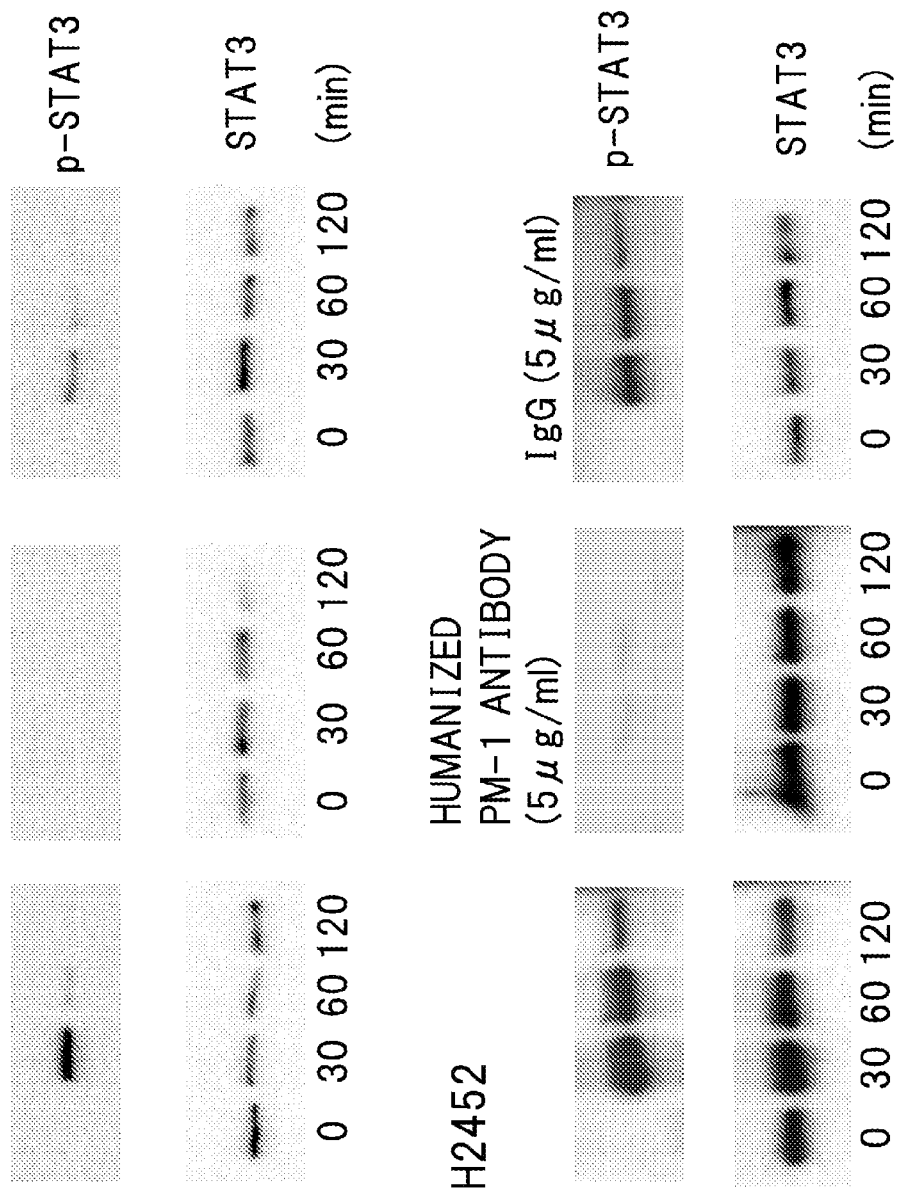
FIG. 16 is a graph that shows the results of Example 13, wherein phosphorylation of STAT3 induced by IL-6/soluble IL-6R stimulation in the cell lines H2052 and H2452 is inhibited by humanized PM-1 antibody.

A study was made to determine whether STAT3 phosphorylation induced by stimulation by IL-6 (10 ng/ml) and soluble IL-6 receptor (100 ng/ml) is inhibited by 5 µg/ml of anti-IL-6 receptor antibody in cell line H2052 and cell line H2452 that produce VEGF. Those results are shown in FIG. 16. As a result, anti-IL-6 receptor antibody significantly inhibited phosphorylated STAT3 (p-STAT3) induced by IL-6/sIL-6R stimulation in malignant mesothelioma cells. On the other hand, significant inhibition of the phosphorylation of STAT3 was not observed in the case of adding the same concentration of human IgG1 (Sigma) as a control instead of anti-IL-6 receptor antibody.

Example 14

Effect of Anti-VEGF Antibody on Growth of Malignant Mesothelioma Cells

Cells of cell line H2052 and cell line H226 were disseminated in a 96-well plate at 500 cells/plate in RPMI medium containing 10% FCS, followed by culturing in five series for 6-7 days in the presence of IL-6 (10 ng/ml) and recombinant soluble IL-6 receptor (100 ng/ml) and in the presence of 1 µg/ml of anti-VEGF antibody.

Figure 17:
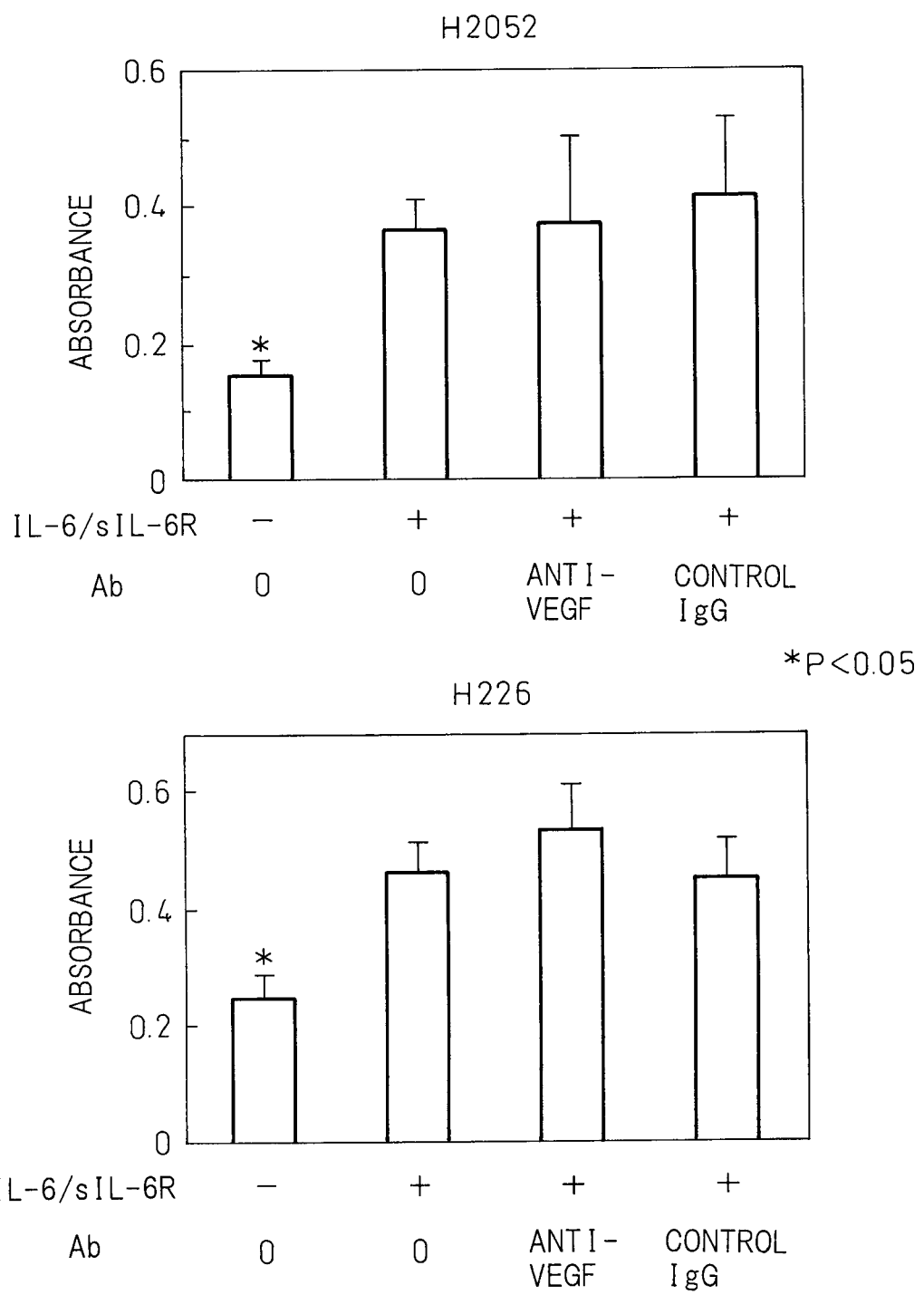
FIG. 17 is a graph that shows the results of Example 14, wherein promotion of the growth of the cell lines H2052 and H226 by IL-6 and soluble IL-6R stimulation is not inhibited by anti-VEGF antibody.

After culturing, the amounts of growth were examined by MTS assay. The same concentration of human IgG1 (Sigma) was used for the control instead of anti-VEGF antibody. Those results are shown in FIG. 17. As a result, anti-VEGF antibody did not inhibit cell growth induced by IL-6/sIL-6R stimulation. On the basis of this result, growth action on malignant mesothelioma cells induced by IL-6/sIL-6R stimulation was clearly determined to not be mediated by VEGF.

Reference Example 1

Preparation of Human Soluble IL-6 Receptor

Soluble IL-6 receptor was produced by PCR using a plasmid pBSF2R.236 that contains DNA encoding IL-6 receptor obtained according to the method of Yamasaki, et al. (Yamasaki, K. et al., Science (1988) 241, 825-828). Plasmid pBSF2R.236 was then digested with restrictase SphI to obtain IL-6 receptor cDNA which was then inserted into mp18 (Amersham). A mutation was introduced into the IL-6 receptor cDNA by PCR with the In Vitro Mutagenesis System (Amersham) using a synthetic oligoprimer designed so as to insert a stop codon into the IL-6 receptor cDNA. As a result of this procedure, a stop codon was inserted at the location of amino acid 345, and cDNA was obtained that encodes soluble IL-6 receptor.

In order to express the cDNA encoding soluble IL-6 receptor in CHO cells, it was coupled with plasmid pSV (Pharmacia) to obtain plasmid pSVL344. Soluble IL-6 receptor cDNA severed with HindIII-SalI was then inserted into plasmid pECEdhfr containing dhfr cDNA to obtain CHO cell expression plasmid pECEdhfr344.

10 µg of plasmid pECEdhfr344 were then used to transfect dhfr-CHO cell line DXB-11 (Urlaub, G. et al., Proc. Natl. Acad. Sci. USA (1980) 77, 4216-4220) according to the calcium phosphate precipitation method (Chen, C. et al., Mol. Cell. Biol. (1987) 7, 2745-2751). The transfected CHO cells were then cultured for 3 weeks in nucleoside-free αXMEM selective culture liquid containing 1 mM glutamine, 10% dialyzed FCS, 100 U/ml of penicillin and 100 µg/ml of streptomycin.

The selected CHO cells were then screened by a limiting dilution method to obtain a single CHO cell clone. This CHO cell clone was amplified with methotrexate at a concentration from 20 nM to 200 nM to obtain human soluble IL-6 receptor-producing CHO cell line 5E27. CHO cell line 5E27 was cultured in Iscove's Modified Dulbecco's Medium (IMDM, Gibco) containing 5% FBS. After recovering the culture supernatant, the concentration of soluble IL-6 receptor in the culture supernatant was measured by ELISA. As a result, soluble IL-6 receptor was confirmed to be present in the culture supernatant.

Reference Example 2

Preparation of Anti-Human IL-6 Antibody

A BALB/c mouse was immunized with 10 µg of recombinant IL-6 (Hirano, T. et al., Immunol. Lett. (1988) 17, 41) together with Freund's complete adjuvant, and this was continued once a week until anti-IL-6 antibody was able to be detected in the serum. Immunocytes were excised from local lymph nodes and fused with myeloma cell line P3U1 using polyethylene glycol 1500. A hybridoma was selected according to the method of Oi, et al. using HAT culture liquid (Selective Methods in Cellular Immunology, W. H. Freeman and Co., San Francisco, 351, 1980) to establish a hybridoma that produced anti-human IL-6 antibody.

An IL-6 binding assay was performed in the manner described below on the hybridoma that produced anti-human IL-6 antibody. Namely, a flexible polyvinyl 96-well microplate (Dynatech Laboratories, Alexandria, Va.) was coated overnight at 4° C. with 100 µl of goat anti-mouse Ig (10 µg/ml, Cooper Biomedical, Malvern, Pa.) in 0.1 M carbonate-hydrogen carbonate buffer (pH 9.6). Next, the plate was treated for 2 hours at room temperature with 100 µl of PBS containing 1% bovine serum albumin (BSA).

After washing the plate with PBS, 100 µl of hybridoma culture supernatant were added to each well followed by incubating overnight at 4° C. The plate was washed and $^{125}$I-labeled recombinant IL-6 was added to each well at 2000 cpm/0.5 ng/well followed by measuring the radioactivity of each well after washing using a gamma counter (Beckman Gamma 9000, Beckman Instruments, Fullerton, Calif.). 32 of 216 hybridoma clones were positive according to the IL-6 binding assay. Stable MH166.BSF2 was ultimately obtained from these clones. The anti-IL-6 antibody MH166 produced by said hybridoma had IgG1κ subtype.

Next, neutralizing activity on hybridoma growth by MH166 antibody was investigated using IL-6-dependent mouse hybridoma clone MH60.BSF2. MH60.BSF2 cells were divided among the wells of a microplate at $1 \times 10^4/200$ µl/well followed by the addition of sample containing MH166 antibody and culturing for 48 hours, and then additionally culturing for 6 hours after adding $^3$H-thymidine (New England Nuclear, Boston, Mass.) at 0.5 µCi/well. The cells were then placed on glass filter paper and treated with an automatic harvester (Labo Mash Science, Tokyo, Japan). Rabbit anti-IL-6 antibody was used for the control.

As a result, MH166 antibody volume-dependently inhibited uptake of $^3$H-thymidine by MH60.BSF2 cells induced by IL-6. Thus, MH166 antibody was clearly demonstrated to neutralize IL-6 activity.

Reference Example 3

Preparation of Anti-Human IL-6 Receptor Antibody

Anti-IL-6 receptor antibody MT18 produced according to the method of Hirata, et al. (Hirata, Y. et al., J. Immunol. (1989) 143, 2900-2906) was bound to activated Sepharose 4B (Pharmacia Fine Chemicals, Piscataway, N.J.) according to attached protocol to purify IL-6 receptor (Yamasaki, K. et al., Science (1988) 241, 825-828). Human myeloma cell line U266 was solubilized with p-paraminophenyl methane sulfonyl fluoride hydrochloride (Wako Chemicals) containing 1% digitonin (Wako Chemicals), 10 mM triethanol amine (pH 7.8) and 0.15 M NaCl (digitonin buffer), and then mixed with MT18 antibody bound to Sepharose 4B beads. Subsequently, the beads were washed six times with digitonin buffer to obtain partially purified IL-6 receptor for immunization.

A BALB/c mouse was immunized four times every 10 days with the aforementioned partially purified IL-6 receptor obtained from $3 \times 10^9$ U266 cells followed by production of hybridoma in accordance with ordinary methods. The binding activity of hybridoma culture supernatant from positive growth wells to IL-6 receptor was investigated according to the method described below. $5 \times 10^7$ U266 cells were labeled with $^{35}$S-methionine (2.5 mCi) and solubilized with the aforementioned digitonin buffer. The solubilized U266 cells were then mixed with MT18 antibody bound to Sepharose 4B beads having a volume of 0.04 ml followed by washing six times with digitonin buffer, eluting the $^{35}$S-methionine-labeled IL-6 receptor with 0.25 ml of digitonin buffer (pH 3.4) and neutralizing with 0.025 ml of 1 M Tris (pH 7.4). 0.05 ml of hybridoma culture supernatant were mixed with 0.01 ml of Protein G Sepharose (Pharmacia). After washing, the Sepharose was incubated with 0.005 ml of $^{35}$S-methionine-labeled IL-6 receptor solution prepared as described above. The immunoprecipitate was then analyzed with SDS-PAGE and hybridoma culture supernatant that reacts with IL-6 receptor was investigated. As a result, reaction-positive hybridoma clone PM-1 (FERM BP-2998) was established. Antibody produced from hybridoma PM-1 have the IgG1κ subtype.

The IL-6 binding inhibitory activity of antibody produced by hybridoma PM-1 on human IL-6 receptor was investigated using human myeloma cell line U266. Human recombinant IL-6 was prepared from E. coli (Hirano, T. et al., Immunol. Lett. (1988) 17, 41-45) and labeled with $^{125}$I using Bolton-Hunter reagent (New England Nuclear, Boston, Mass.) (Taga, T. et al., J. Exp. Med. (1987) 166, 967-981).

$4 \times 10^5$ U266 cells were cultured with 70% (v/v) hybridoma PM-1 culture supernatant and 14000 cpm of $^{125}$I-labeled IL-6 for 1 hour. 70 µl of sample were layered onto 300 µl of FCS in a 400 µl microfuge polyethylene tube followed by centrifugation and measurement of radioactivity of the cells.

As a result, antibody produced by hybridoma PM-1 was clearly determined to inhibit binding of IL-6 to IL-6 receptor.

Reference Example 4

Preparation of Anti-Mouse IL-6 Receptor Antibody

Monoclonal antibody to mouse IL-6 receptor was prepared according to the method described in Saito, T. et al., J. Immunol. (1991) 147, 168-173.

CHO cells producing mouse soluble IL-6 receptor were cultured in IMDM culture liquid containing 10% FCS followed by purification of mouse soluble IL-6 receptor from the culture supernatant using an affinity column in which anti-mouse IL-6 receptor antibody RS12 (refer to the aforementioned Saito, T. et. al.) was immobilized in Affigel 10 gel (BioRad).

50 µg of the resulting mouse soluble IL-6 receptor were mixed with Freund's complete adjuvant and injected into the abdomen of a Wistar rat. The rat was additionally immunized with Freund's incomplete adjuvant starting two weeks later. Rat spleen cells were then harvested on day 45, and after fusing $2 \times 10^8$ cells with $1 \times 10^7$ cells of mouse myeloma cell line P3U1 using 50% PEG1500 (Boehringer-Mannheim) in accordance with ordinary methods, the fused cells were screened for hybridoma with HAT medium.

After adding hybridoma culture supernatant to a plate coated with rabbit anti-rat IgG antibody (Cappel), the mouse soluble IL-6 receptor was allowed to react. Next, hybridoma that produced antibody to mouse soluble IL-6 receptor was screened by ELISA using rabbit anti-mouse IL-6 receptor antibody alkaline phosphatase-labeled sheep anti-rabbit IgG. The hybridoma clones that were confirmed to produce antibody were sub-screened twice to obtain a single hybridoma clone. That clone was named MR16-1.

The neutralizing activity during information transmission by mouse IL-6 of this hybridoma-producing antibody was investigated according to the uptake of $^3$H-thymidine using MH60.BSF2 cells (Matsuda, T. et al., J. Immunol. (1988) 18, 951-956). $1 \times 1$ cells/200 µl/well of MH60.BSF2 cells were prepared in a 96-well plate. 10 pg/ml of mouse IL-6 and 12.3 to 1000 ng/ml of MR16-1 antibody or RS12 antibody were added to this plate and cultured for 44 hours at 37° C. and 5% $CO_2$ followed by the addition of 1 µCi/well of $^3$H-thymidine. The uptake of 3H-thymidine was then measured 4 hours later. As a result, MR16-1 antibody inhibited the uptake of $^3$H-thymidine by MH60.BSF2 cells.

Thus, antibody produced by hybridoma MR16-1 (FERM BP-5875) was clearly determined to inhibit binding of IL-6 to IL-6 receptor.

What is claimed is:

1. A method of treating mesothelioma, comprising administering an interleukin-6 (IL-6) antagonist to a patient in need thereof, wherein the IL-6 antagonist is a monoclonal antibody to an IL-6 receptor selected from PM-1 and MR16-1.

2. The method of claim 1, wherein the mesothelioma is pleural mesothelioma.

3. The method of claim 2, wherein the mesothelioma is malignant pleural mesothelioma.

4. The method of claim 1, wherein the monoclonal antibody is a monoclonal antibody to a human IL-6 receptor.

5. The method of claim 4, wherein the monoclonal antibody is a PM-1 antibody.

6. The method of claim 1, wherein the monoclonal antibody is a monoclonal antibody to a mouse IL-6 receptor.

7. The method of claim 6, wherein the monoclonal antibody is a MR16-1 antibody.

8. The method of claim 1, wherein the monoclonal antibody is a chimeric antibody, or humanized antibody.

9. The method of claim 8, wherein the monoclonal antibody is a humanized PM-1 antibody.

10. The method of claim 1, wherein the antibody is administered in a pharmaceutically acceptable carrier.

11. The method of claim 1, wherein the antibody is administered in an amount of 0.01 to 1000 mg per kg of body weight per administration.

12. The method of claim 11, wherein the antibody is administered in an amount of 5 to 50 mg per kg of body weight per administration.

13. A method of inhibiting the growth of a mesothelioma cell, comprising administering an IL-6 antagonist to a patient in need thereof, wherein the antagonist is a monoclonal antibody to an IL-6 receptor selected from PM-1 and MR16-1.

14. The method of claim 13, wherein the mesothelioma is pleural mesothelioma.

15. The method of claim 14, wherein the mesothelioma is malignant pleural mesothelioma.

16. The method of claim 13, wherein the monoclonal antibody is a monoclonal antibody to a human IL-6 receptor.

17. The method of claim 16, wherein the monoclonal antibody is a PM-1 antibody.

18. The method of claim 13, wherein the monoclonal antibody is a monoclonal antibody to a mouse IL-6 receptor.

19. The method of claim 18, wherein the monoclonal antibody is a MR16-1 antibody.

20. The method of claim 13, wherein the monoclonal antibody is a chimeric antibody, or humanized antibody.

21. The method of claim 20, wherein the monoclonal antibody is a humanized PM-1 antibody.

22. The method of claim 13, wherein the antibody is administered in a pharmaceutically acceptable carrier.

23. The method of claim 13, wherein the antibody is administered in an amount of 0.01 to 1000 mg per kg of body weight per administration.

24. The method of claim 23, wherein the antibody is administered in an amount of 5 to 50 mg per kg of body weight per administration.

25. A method of treating mesothelioma, comprising administering a mesothelioma therapeutic agent to a patient in need thereof, wherein the agent comprises an IL-6 antagonist and a pharmaceutically acceptable carrier, and wherein the antagonist is an monoclonal antibody to an IL-6 receptor selected from PM-1 and MR16-1.

26. The method of claim 25, wherein the pharmaceutically acceptable carrier is selected from the group consisting of water, pharmaceutically acceptable organic solvents, collagen, polyvinyl alcohol, polyvinyl pyrrolidone, carboxyvinyl polymer, sodium carboxymethyl cellulose, sodium polyacrylate, sodium arginate, water-soluble dextran, sodium carboxymethyl starch, pectin, methyl cellulose, ethyl cellulose xanthan gum, gum Arabic, casein, gelatin, agar, diglycerin, propylene glycol, polyethylene glycol, petroleum jelly, paraffin, stearyl alcohol, stearic acid, human serum albumin, mannitol, sorbitol, lactose arid surfactants.

27. The method of treating mesothelioma according to claim 1, wherein an amount of the antibody to an IL-6 receptor administered to a patient in need thereof is sufficient to inhibit the cell growth of mesothelioma cells.

* * * * *